(12) United States Patent
Zhang et al.

(10) Patent No.: US 9,370,640 B2
(45) Date of Patent: Jun. 21, 2016

(54) STEERABLE MEDICAL GUIDE WIRE DEVICE

(71) Applicant: Strategic Polymer Sciences, Inc., State College, PA (US)

(72) Inventors: Shihai Zhang, State College, PA (US); Stephen Davis, Swansea, SC (US); Mark Levatich, State College, PA (US); Richard Ducharme, Alexandria, PA (US)

(73) Assignee: Novasentis, Inc., State College, PA (US)

( * ) Notice: Subject to any disclaimer, the term of this patent is extended or adjusted under 35 U.S.C. 154(b) by 0 days.

(21) Appl. No.: 13/734,866

(22) Filed: Jan. 4, 2013

(65) Prior Publication Data

US 2013/0123692 A1 May 16, 2013

Related U.S. Application Data

(60) Continuation-in-part of application No. 13/482,901, filed on May 29, 2012, now abandoned, which is a division of application No. 11/898,472, filed on Sep. 12, 2007, now abandoned.

(51) Int. Cl.
*A61M 25/01* (2006.01)
*A61M 25/09* (2006.01)
*A61M 25/00* (2006.01)

(52) U.S. Cl.
CPC ..... *A61M 25/0158* (2013.01); *A61M 25/09041* (2013.01); *A61M 25/0045* (2013.01); *A61M 2025/0042* (2013.01); *A61M 2025/0058* (2013.01); *A61M 2025/0063* (2013.01); *A61M 2025/0915* (2013.01)

(58) Field of Classification Search
CPC ................ A61B 2017/003; A61M 2025/0058; A61M 20/0105
USPC ......... 600/114, 117, 143, 145, 146, 151, 152; 604/95.01; 606/1
See application file for complete search history.

(56) References Cited

U.S. PATENT DOCUMENTS

| 5,350,966 A | 9/1994 | Culp |
| 6,071,234 A | 6/2000 | Takada |
| 6,144,547 A | 11/2000 | Retseptor |
| 6,160,084 A | 12/2000 | Langer et al. |

(Continued)

FOREIGN PATENT DOCUMENTS

| JP | 2010283926 A | 12/2010 |
| JP | 2011172339 A | 9/2011 |

(Continued)

OTHER PUBLICATIONS

Paul Brochu et al., "Advances in Dielectric Elastomers for Actuators and Artificial Muscles," Macromolecular Journals, Macromolecular Rapid Communications, Oct. 27, 2009, pp. 10-36, Wiley-VCH Verlag GmbH & Co. KGaA, Weinheim.

(Continued)

*Primary Examiner* — Aaron Roane
(74) *Attorney, Agent, or Firm* — Edward C. Kwok; Hogan Lovells US LLP

(57) ABSTRACT

A steerable guide wire including one or more electroactive polymer layers, wherein each EAP layer is disposed between a layer of a first electrode and a layer of a plurality of second electrodes.

20 Claims, 16 Drawing Sheets

(56) References Cited

U.S. PATENT DOCUMENTS

| | | | |
|---|---|---|---|
| 6,183,435 B1 | 2/2001 | Bumbalough et al. | |
| 6,278,084 B1 | 8/2001 | Maynard | |
| 6,376,971 B1 | 4/2002 | Pelrine et al. | |
| 6,385,472 B1 | 5/2002 | Hall et al. | |
| 6,423,412 B1 | 7/2002 | Zhang et al. | |
| 6,514,237 B1 | 2/2003 | Maseda | |
| 6,605,246 B2 | 8/2003 | Zhang et al. | |
| 6,679,836 B2 * | 1/2004 | Couvillon, Jr. | 600/146 |
| 6,703,257 B2 | 3/2004 | Takeuchi et al. | |
| 6,770,081 B1 | 8/2004 | Cooper et al. | |
| 6,787,238 B2 * | 9/2004 | Zhang et al. | 428/421 |
| 6,809,462 B2 | 10/2004 | Pelrine et al. | |
| 6,812,624 B1 * | 11/2004 | Pei et al. | 310/309 |
| 6,852,416 B2 | 2/2005 | Zhang et al. | |
| 6,877,325 B1 | 4/2005 | Lawless | |
| 6,888,291 B2 | 5/2005 | Arbogast et al. | |
| 6,891,317 B2 | 5/2005 | Pei et al. | |
| 6,921,360 B2 | 7/2005 | Banik | |
| 6,939,338 B2 | 9/2005 | Waldhauser et al. | |
| 6,969,395 B2 | 11/2005 | Eskuri | |
| 6,979,312 B2 | 12/2005 | Shimada | |
| 6,997,870 B2 | 2/2006 | Couvillon, Jr. | |
| 7,038,357 B2 | 5/2006 | Goldenberg et al. | |
| 7,078,101 B1 | 7/2006 | Ramotowski et al. | |
| 7,097,615 B2 | 8/2006 | Banik et al. | |
| 7,128,707 B2 | 10/2006 | Banik | |
| 7,199,501 B2 | 4/2007 | Pei et al. | |
| 7,224,106 B2 | 5/2007 | Pei et al. | |
| 7,261,686 B2 | 8/2007 | Couvillon, Jr. | |
| 7,339,572 B2 | 3/2008 | Schena | |
| 7,368,862 B2 | 5/2008 | Pelrine et al. | |
| 7,567,681 B2 | 7/2009 | Pelrine et al. | |
| 7,766,896 B2 | 8/2010 | Kornkven Volk et al. | |
| 7,839,647 B2 | 11/2010 | Lee et al. | |
| 7,909,844 B2 | 3/2011 | Alkhatib et al. | |
| 7,952,261 B2 | 5/2011 | Lipton et al. | |
| 7,971,850 B2 | 7/2011 | Heim et al. | |
| 8,126,534 B2 | 2/2012 | Maschke | |
| 8,222,799 B2 | 7/2012 | Polyakov et al. | |
| 8,362,882 B2 | 1/2013 | Heubel et al. | |
| 8,384,271 B2 | 2/2013 | Kwon et al. | |
| 8,390,594 B2 | 3/2013 | Modarres et al. | |
| 8,398,693 B2 | 3/2013 | Weber et al. | |
| 8,414,632 B2 | 4/2013 | Kornkven Volk et al. | |
| 8,564,181 B2 | 10/2013 | Choi et al. | |
| 2001/0051769 A1 | 12/2001 | Hoek et al. | |
| 2003/0065373 A1 | 4/2003 | Lovett et al. | |
| 2004/0138733 A1 | 7/2004 | Weber et al. | |
| 2005/0065400 A1 | 3/2005 | Banik et al. | |
| 2006/0025809 A1 | 2/2006 | Shelton, IV | |
| 2006/0047302 A1 | 3/2006 | Ortiz et al. | |
| 2006/0064055 A1 | 3/2006 | Pile-Spellman et al. | |
| 2006/0129130 A1 | 6/2006 | Tal et al. | |
| 2006/0293643 A1 | 12/2006 | Wallace et al. | |
| 2007/0032851 A1 | 2/2007 | Shippy, III et al. | |
| 2007/0043338 A1 | 2/2007 | Moll et al. | |
| 2007/0060997 A1 | 3/2007 | De Boer | |
| 2007/0123750 A1 | 5/2007 | Baumgartner et al. | |
| 2007/0200467 A1 | 8/2007 | Heydt et al. | |
| 2009/0002205 A1 | 1/2009 | Klinghult et al. | |
| 2010/0079264 A1 | 4/2010 | Hoellwarth | |
| 2010/0090813 A1 | 4/2010 | Je et al. | |
| 2010/0316242 A1 | 12/2010 | Cohen et al. | |
| 2011/0038625 A1 | 2/2011 | Zellers et al. | |
| 2011/0133598 A1 | 6/2011 | Jenninger et al. | |
| 2011/0290686 A1 | 12/2011 | Huang | |
| 2012/0105333 A1 | 5/2012 | Maschmeyer et al. | |
| 2012/0126663 A1 | 5/2012 | Jenninger et al. | |
| 2012/0126959 A1 | 5/2012 | Zarrabi et al. | |
| 2012/0128960 A1 | 5/2012 | Bugen et al. | |
| 2012/0178880 A1 | 7/2012 | Zhang et al. | |
| 2012/0194448 A1 | 8/2012 | Rothkopf | |
| 2012/0206248 A1 | 8/2012 | Biggs | |
| 2012/0223880 A1 | 9/2012 | Birnbaum et al. | |
| 2012/0239032 A1 | 9/2012 | Zhang et al. | |
| 2013/0123692 A1 | 5/2013 | Zhang et al. | |
| 2013/0207793 A1 | 8/2013 | Weaber et al. | |
| 2014/0035735 A1 | 2/2014 | Zellers et al. | |
| 2014/0085065 A1 | 3/2014 | Biggs et al. | |
| 2014/0090424 A1 | 4/2014 | Charbonneau et al. | |
| 2014/0139328 A1 | 5/2014 | Zellers et al. | |
| 2014/0139329 A1 | 5/2014 | Ramstein et al. | |
| 2014/0139436 A1 | 5/2014 | Ramstein et al. | |
| 2014/0140551 A1 | 5/2014 | Ramstein | |
| 2014/0191973 A1 | 7/2014 | Zellers et al. | |
| 2015/0065953 A1 | 3/2015 | Ducharme et al. | |

FOREIGN PATENT DOCUMENTS

| | | |
|---|---|---|
| JP | 2012134998 A | 7/2012 |
| KR | 20060107259 A | 10/2006 |
| KR | 20110110212 A | 10/2011 |
| KR | 20120013273 A | 2/2012 |
| KR | 20120063318 A | 6/2012 |
| KR | 20120078529 A | 7/2012 |
| KR | 20120105785 A | 9/2012 |
| WO | WO2007102939 | 9/2007 |
| WO | WO2008016403 | 2/2008 |
| WO | 2010/085575 A1 | 7/2010 |

OTHER PUBLICATIONS

Mazzoldi et al., "Conductive Polymer Based Structures for a Steerable Catheter," Smart Structures and Materials 2000: Electroactive Polymer Actuators and Devices, 2000, pp. 273-280 vol. 398.

Arai et al., "Intelligent Assistance in Operation of Active Catheter for Minimum Invasive Surgery," IEEE International Workshop on Robot and Human Communication, 1994, pp. 192-197.

Fukuda, "Micro Active Catheter System with Multi Degrees of Freedom," IEEE, 1994, pp. 2290-2295.

Guo et al, "Micro Active Guide Wire Catheter System" IEEE, 1995, pp. 172-177.

Della Sana, "Intravascular Mictrocatheters Steered by Conducting Polymer Actuators," 18th Annual International Conference of the IEEE Engineering in Medicine and Biology Society, Amsterdam, 1996, pp. 2203-2204.

Guo, Micro Active Catheter Using ICPF Actuator; Characteristic Evaluation, Electrical Model and Operability Evaluation, IEEE, 1996, pp. 1312-1317.

Guo, "Micro Active Guide Wire Catheter Using ICPF Actuator" AMC 1996-MIE, IEEE, 1996, pp. 729-734.

Guo, Micro Catheter System and Active Guide Wire, IEEE International Conference on Robotics and Automation, 1995, pp. 79-84.

Bar-Cohen, "Chapter 10: Artificial Muscle Using Electroactive Polymers," Biomimetics: Biologically Inspired Technologies, CRC Taylor & Francis Group, Boca Raton, 2005, pp. 267-290.

Spinks et al., "Strain Response from Polypyrrole Actuators Under Load," Advanced Functional Materials, 12.6+7, 2002, pp. 437-440.

International Search Report and the Written Opinion of the International Searching Authority Issued in International Application No. PCT/US2008/070450, dated on Nov. 7, 2008.

International Search Report and Written Opinion for PCT/US2014/010219, date of mailing May 23, 2014, 20 pgs.

Matysek, Marc et al., "Combined Driving and Sensing Circuitry for Dielectric Elastomer Actuators in mobile applications", Electroactive Polymer Actuators and Devices (EAPAD) 2011, Proc. of SPIE vol. 7976, 797612, 11 pages.

Neese, Bret et al., "Large Electrocaloric Effect in Ferroelectric Polymers Near Room Temperature", Science vol. 321, Aug. 8, 2008, pp. 821-823.

Zhang Q. M. et al., "Giant Electrostriction and Relaxor Ferroelectric Behavior in Electron-Irradiated Poly(vinylidene fluoride-trifluoroethylene) Copolymer", Science vol. 280, Jun. 26, 1998, pp. 2101-2104.

Xia F. et al., "High Electromechanical Responses in a Poly(vinylidene fluoride-trifluoroethylene-chlorofluoroethylene) Terpolymer", Advanced Materials, vol. 14, Issue 21, Nov. 2002, pp. 1574-1577.

(56) References Cited

OTHER PUBLICATIONS

PCT International Search Report and Written Opinion date of mailing Dec. 23, 2013, International Application No. PCT/US2013/053594, 9 pages.
PCT International Search Report and Written Opinion date of mailing Mar. 17, 2014, International Application No. PCT/US2013/071085, 10 pages.
PCT International Search Report and Written Opinion date of mailing Mar. 13, 2014, International Application No. PCT/US2013/071072, 15 pages.
PCT International Search Report and Written Opinion date of mailing Mar. 20, 2014, International Application No. PCT/US2013/071075, 12 pages.
PCT International Search Report and Written Opinion date of mailing Mar. 28, 2014, International Application No. PCT/US2013/071078, 13 pages.
PCT International Search Report and Written Opinion date of mailing Apr. 28, 2014, International Application No. PCT/US2013/071062, 11 pages.
PCT International Preliminary Report on Patentability dated May 26, 2015, International Application No. PCT/US2013/071072, 9 pages.
PCT International Preliminary Report on Patentability dated May 26, 2015, International Application No. PCT/US2013/071075, 9 pages.
PCT International Preliminary Report on Patentability dated May 26, 2015, International Application No. PCT/US2013/071078, 10 pages.
PCT International Preliminary Report on Patentability dated May 26, 2015, International Application No. PCT/US2013/071085, 7 pages.
PCT International Preliminary Report on Patentability dated Jul. 7, 2015, International Application No. PCT/IB2013/003212, 15 pages.
PCT International Search Report and Written Opinion date of mailing Oct. 15, 2014, International Application No. PCT/IB2013/003212, 20 pages.
PCT International Search Report and Written Opinion date of mailing Dec. 18, 2014, International Application No. PCT/US2014/053494, 11 pages.
PCT International Preliminary Report on Patentability dated Jul. 7, 2015, International Application No. PCT/US2014/010219, 14 pages.
PCT International Preliminary Report on Patentability for International Application No. PCT/US2014/010219, date of mailing Jul. 16, 2015, 14 pages.

* cited by examiner

STEERABLE MEDICAL GUIDE WIRE DEVICE

CROSS-REFERENCE TO RELATED APPLICATIONS

This is a continuation-in-part of U.S. patent application Ser. No. 13/482,901 filed May 29, 2012, which is a divisional of U.S. patent application Ser. No. 11/898,472 filed Sep. 12, 2007, which are both incorporated herein by reference.

BACKGROUND OF THE INVENTION

Guide wires are commonly utilized in medical procedures to navigate a pathway to a particular location. FIG. 1 illustrates the use of a guide wire. The guide wire 110 is feed into a patient along, a pathway 120 such as a vascular tract or other lumen in the body. A needle or knife is typically used to create an opening to the pathway in a patient if the target body lumen is not externally accessible. The guide wire is then advanced through the pathway to a target location in the patient. Once the guide wire reaches the target location, a catheter, stent or other medical device may be guided to the target location by the guide wire. For example, a catheter may be fed over the base of the guide wire and then advanced up the guide wire to the target location. The guide wire improves access to treatment locations within the patient body. However, current guide wires have limited steering capability and are typically very flexible. The high degree of flexibility is helpful to avoid causing trauma to surrounding tissue but may make it difficult to introduce the guide wire into the pathway and advance the guide wire along sections of the pathway.

The conventional techniques for steering guide wires limit their application. Similarly, the width (e.g., diameter) of conventional guide wires may also limit their application. In addition, the flexibility of conventional guide wires may also limit their application. Accordingly there is a continuing need for improved, steerable guide wires. There is also a continuing need for steerable guide wires that have reduced diameters, increased stiffness, and/or provide other advantages as compared to conventional guide wires.

SUMMARY OF THE INVENTION

The present technology may best be understood by referring to the following description and accompanying drawings that are used to illustrate embodiments of the present technology directed toward steerable medical devices including guide wires, catheters and other percutaneous instruments.

In one embodiment, the medical device includes a guide wire and a drive unit coupled to the guide wire. The guide wire includes one or more layers of a first electrode, one or more layers of a plurality of second electrodes and one or more electroactive polymer (EAP) layers. Each EAP layer is disposed between a layer of a first electrode and a layer of a plurality of second electrodes. The drive unit is adapted to generate one or more potential voltages and to apply each of the one or more potential voltages respectively across one or more sets of the first electrode and the second electrode. The one or more potential voltages can be selectively applied across the EAP layer to steer the guide wire, control the shape of the guide wire, adjust the rigidity of the guide wire, and/or cause one or more portions of the guide wire to vibrate. Alternatively, the medical device may include a catheter or the like and a drive unit. Such medical devices similarly include one or more layers of a first electrode, one or more layers of a plurality of second electrodes and one or more EAP layers In another embodiment, the guide wire, catheter or the like includes a plurality of active EAP portions arranged in multiple stacks. The active EAP portions in each stack are aligned with each other and perpendicular to a longitudinal axis of the guide wire, catheter or the like, in addition, the stacks are arranged along the longitudinal axis of the guide wire, catheter or the like. A drive unit coupled to the guide wire, catheter, or the like generates one or more potential voltages. The drive unit applies the potential voltage across one or more active EAP portions to control one or more physical parameter of the guide wire, catheter or the like. The physical parameters may include the deflection, the rigidity and/or the like of the guide wire, catheter or the like.

This Summary is provided to introduce a selection of concepts in a simplified form that are further described below in the Detailed Description. This Summary is not intended to identify key features or essential features of the claimed subject matter, no is it intended to be used to limit the scope of the claimed subject matter.

BRIEF DESCRIPTION OF THE DRAWINGS

Embodiments of the present technology are illustrated by way of example and not by way of limitation, in the figures of the accompanying drawings and in which like reference numerals refer to similar elements and in which.

DETAILED DESCRIPTION OF THE INVENTION

Figure 1:
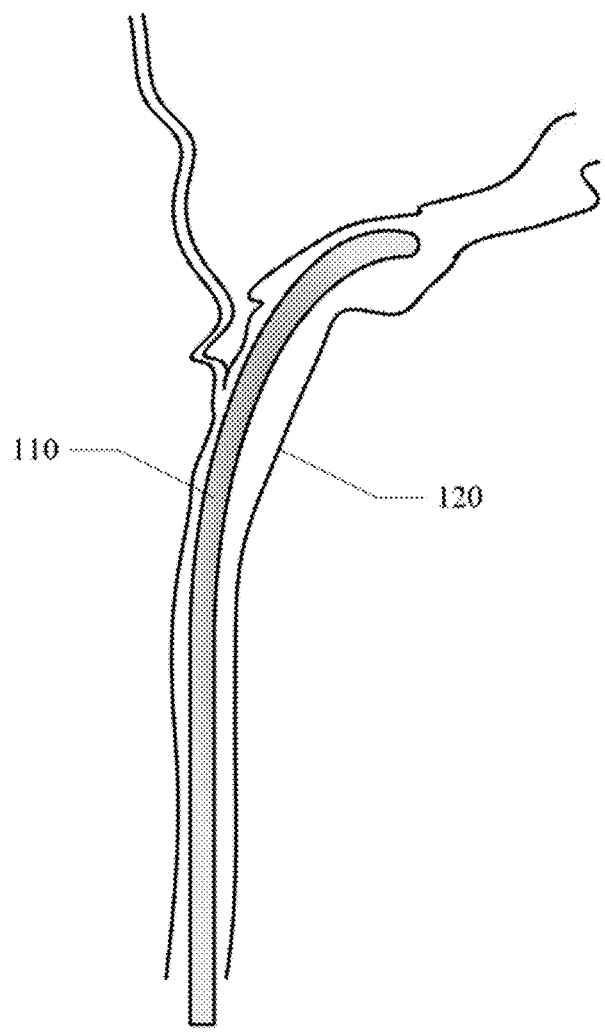
FIG. 1 illustrates the use of a conventional guide wire medical device.

Reference will now be made in detail to the embodiments of the present technology, examples of which are illustrated in the accompanying drawings. While the present technology will be described in conjunction with these embodiments, it will be understood that they are not intended to limit the invention to these embodiments. On the contrary, the invention is intended to cover alternatives, modifications and equivalents, which may be included within the scope of the invention as defined by the appended claims. Furthermore, in the following detailed description of the present technology, numerous specific details are set forth in order to provide a thorough understanding of the present technology. However, it is understood that the present technology may be practiced without these specific details. In other instances, well-known methods, procedures, components, and circuits have not been described in detail as not to unnecessarily obscure aspects of the present technology.

Some embodiments of the present technology which follow are presented in terms of routines, modules, logic blocks, and other symbolic representations of operations on data within one or more electronic devices. The descriptions and representations are the means used by those skilled in the art to most effectively convey the substance of their work to others skilled in the art. A routine, module, logic block and/or the like, is herein, and generally, conceived to be a self-consistent sequence of processes or instructions leading to a desired result. The processes are those including physical manipulations of physical quantities. Usually, though not necessarily, these physical manipulations take the form of electric or magnetic signals capable of being stored, transferred, compared and otherwise manipulated in an electronic device. For reasons of convenience, and with reference to common usage, these signals are referred to as data, bits, values, elements, symbols, characters, terms, numbers, strings, and/or the like with reference to embodiments of the present technology.

It should be borne in mind, however, that all of these terms are to be interpreted as referencing physical manipulations and quantities and are merely convenient labels and are to be interpreted further in view of terms commonly used in the art. Unless specifically stated otherwise as apparent from the following discussion, it is understood that through discussions of the present technology, discussions utilizing the terms such as "receiving," and/or the like, refer to the actions and processes of an electronic device such as an electronic computing device, that manipulates and transforms data. The data is represented as physical (e.g., electronic) quantities within the electronic device's logic circuits, registers, memories and/or the like, and is transformed into other data similarly represented as physical quantities within the electronic device.

In this application, the use of the disjunctive is intended to include the conjunctive. The use of definite or indefinite articles is not intended to indicate cardinality. In particular, a reference to "the" object or "a" object is intended to denote also one of a possible plurality of such objects. It is also to be understood that the phraseology and terminology used herein is for the purpose of description and should not be regarded as limiting.

Figure 2:
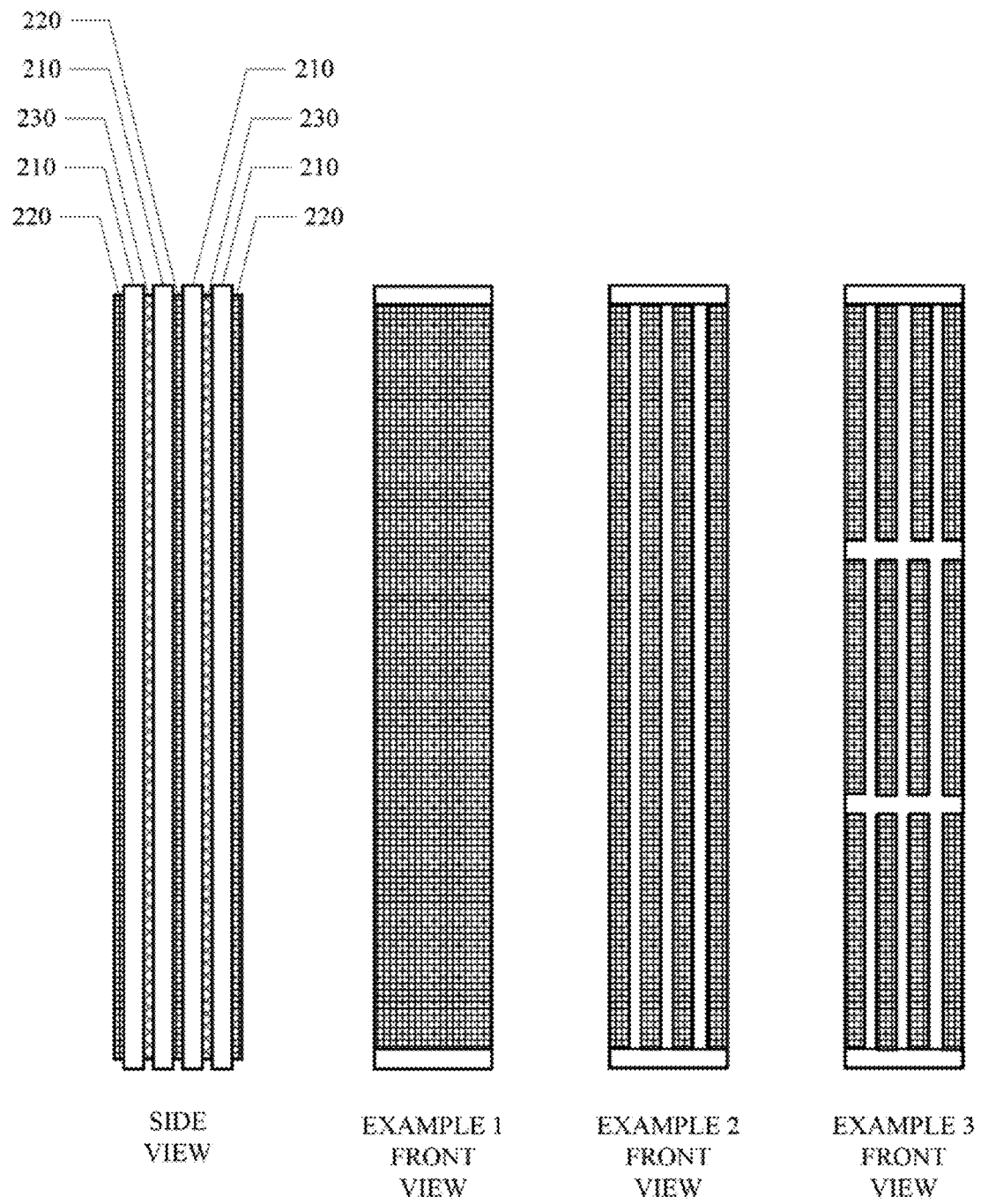
FIG. 2 shows a block diagram of a guide wire medical device, in accordance with one embodiment of the present technology.

Referring now to FIG. 2, a guide wire medical device, in accordance with one embodiment of the present technology, is shown. The guide wire has an elongated form factor of a flexible rod, wherein the longitudinal dimension of the guide wire is substantially larger than the other dimensions, such as diameter or width, of the form factor. The dimension of the guide wire form factor are adapted for use in one or more body lumens within one or more living organism. The guide wire or one or more components of the guide wire may include a lumen. In other embodiments, the guide wire may not have any lumens. Although embodiments of the present technology are disclosed herein with reference to a guide wire, embodiments of the present technology may also be applied to other medical devices such as catheters or the like.

The guide wire includes a plurality of electroactive polymer (EAP) layers 210, a plurality of first electrodes 220 and a plurality of second electrodes 230. The EPA layers and first and second electrode layers are coupled together as an EAP construct. The various layers of EAP, first and second electrodes, along with optional layers such as insulator, sheath and the like layers may be coupled directly to each other or may be coupled together by an appropriate adhesive. It is to be appreciated that the illustrated guide wire is not to scale. The guide wire may be approximately 2-500 centimeters (cm) in length. The guide wire may be approximately 0.2-5 millimeter (mm) in diameter or width. The first and second electrodes are typically $\frac{1}{10}$-$\frac{1}{50}$ the thickness of the EAP layers. The first and second electrodes may be a conductive polymer, a metal such as gold or platinum, or alloys thereof.

Each EAP layer is disposed between layers of a first electrode and a second electrode. The use of the term "disposed between" herein is intended to include directly and indirectly between. In one embodiment, each EAP layer may be between respective layers of a first electrode and a second electrode. For example, the guide ware may include a first EAP layer between a first one of a first electrode and a first one of a second electrode, a second EAP layer may be between a second one of the first electrode and a second one of the second electrode, and so on. In another embodiment, adjacent EAP layers may share the same electrode between the two EAP layers to reduce the number of electrode layers. For example, the guide wire may include a first EAP layer between a first one of a first electrode and a first one ala second electrode as illustrated in the Side View of FIG. 2. A second EAP layer may be between the first one of the second electrode and a second one of the first electrode. A third EAP may be between the second one of the first electrode and a second one of the second electrode.

In another embodiment, one or more EAP layers may be between a first number of layers of a first electrode and a second number of layers of a second electrode. For example, a first EAP layer may be between a first one of a first electrode and a first one of second electrode. A second EAP layer may be between a second one of the first electrode and the first one of the first electrode. The second EAP layer in such case will also be indirectly between the second one of the first electrode and the first one of the second electrode. A third EAP layer may be between a third one of the first electrode and the second one of the first electrode. Again, the third EAP layer in such case will also be indirectly between third one of the first electrode and the first one of the second electrode.

The plurality of EAP layers, in accordance with embodiments of the present technology, are disposed between one or more layers of a first electrode and one or more layers of a second electrode such that when a potential voltage is applied between the first electrode and second electrode an electric field is applied across the plurality of EAP layers.

In one embodiment, the EAP layer may be an electrostrictive relaxor ferroelectric EAP. In one implementation, the electrostrictive relaxor ferroelectric EAP layer may be a ter-polymer including at least one monomer of vinylidene-fluoride, at least one monomer selected from the group consisting of trifluoroethylene and tetrafluoroethylene, and at least one monomer selected from the group consisting of tetrafluoroethylene, vinyl fluoride, perfluoro (methyl vinyl ether), bromotrifluorethylene, chlorofluoroethylene, chlorotrifluoroethylene, and hexafluoropropylene. In one implementation, the ter-polymer may be a polyvinylidene fluoride (PVDF) such as $P(VDF_x\text{-}TrFE_y\text{-}CFE_{1-x-y})$, $P(VDF_x\text{-}TrFE_y\text{-}CTFE_{1-x-y})$, poly $(VDF_x\text{-}TrFE_y\text{-}vinylidene\ chloride_{1-x-y})$, poly(vinylidene fluoride-tetrafluoroethylene-chlorotrifluoroethylene), poly (vinylidene fluoride-trifluoroethylene-hexafluoropropylene), poly(vinylidenefluoride-tetrafluoroethylene-hexafluoropropylene), poly(vinylidene fluoride-trifluoroethylene-tetrafluoroethylene), poly(vinylidene fluoride-tri fluoroethylene-vinyl fluoride), poly(vinylidene fluoride-tetrafluoroethylene-vinyl fluoride), poly(vinylidene fluoride-trifluoroethylene-perfluoro(methyl vinyl ether)), poly (vinylidene fluoride-tetrafluoroethylene-perfluoro (methyl vinyl ether)), poly(vinylidenefluoride-trifluoroethylene-bromotrifluoroethylene, polyvinylidene), poly(vinylidene fluoride-tetrafluoroethylene-chlorofluoroethylene), poly(vinylidene fluoride-trifluoroethylene-vinylidene chloride), and poly(vinylidene fluoride-tetrafluoroethylene-vinylidene chloride), and wherein x is in the range from 0.5 to 0.75, and y is in the range 0.45 to 0.2 and x+y is less than 1. In another implementation, the electrostrictive relaxor ferroelectric EAP layer may be an irradiated polyvinylidine fluoride polymer. In one implementation, the irradiated polyvinylidine fluoride polymer may be polyvinylidine fluoride-trifluoroethylene P(VDF-TrFE), polyvinylidine fluoride tetrafluoroethylene P(VDF-TFE), polyvinylidine fluoride trifluoroethylene-hexafluoropropylene P(VDF-TFE-HFE) and polyvinylidine fluoride-hexafluoropropylene P(VDF-HFE).

A thickness strain ($S_3$) of electrostrictive relaxor ferroelectric EAPs of up to 7% or more can be achieved under an applied electric, field of up to approximately 140 megavolts per meter (MV/m). A transverse stain (S1), with respect to the thickness dimension of electrostrictive relaxor ferroelectric EAPs, of up to 5% or more can be achieved for an applied electric field of up to approximately 140 MV/m. In addition, the electrostrictive relaxor ferroelectric EAPs exhibit an elastic modulus of approximately 100 MegaPascals (MPa) or more. The combination of the relatively high elastic modules and relatively high strain results in a high elastic energy, enabling the electrostrictive relaxor ferroelectric EAPs to provide a large range of motion with a high degree of precision.

In one embodiment, each layer of the first and/or second electrode may be a continuous sheet, as illustrated in Example 1 of FIG. 2. The EAP layer disposed between respective first and second electrode layers are active and expand when a voltage potential as applied by the first and second electrode layer across the corresponding EAP layer. In another embodiment, the layers of the first electrode and/or second electrode may be patterned into a plurality of electrodes in each layer, as illustrated in Examples 2 and 3 of FIG. 2. For instance, the layer of first electrodes may be patterned into a plurality of first electrodes. The first and second electrodes may be arranged in a large variety of patterns, including linear patterns, array patterns, geometrically expanding patterns, radial patterns, axial patterns, spiral patterns or other geometries which provide sufficient electric field strengths to achieve a desired electroactive response. The term geometrically expanding pattern means a pattern that when rolled, folded or the like into a guide wire or catheter form factor, the corresponding active portions of the EAP stack on top of each other. Each stack of active EAP effectively forms a respective actuator.

The portions of the EAP layer disposed between respective first and second electrodes are active portions, while those portions that do not have a first and second electrode disposed directly or indirectly on either side of them are inactive. One or more dimensions of the active portions will change as a function of a potential voltage applied to the first and second electrodes across the EAP. In one embodiment the EAP layer may be an electrostrictive relaxor ferroelectric EAP. In one implementation, the electrostrictive relaxor ferroelectric EAP may be formed from a ferroelectric polymer by introducing chloride containing monomers such as chlorofluoroethylene (CFE) and chlorotrifluoroethylene (CTFE) or hexafluoropropylene to the copolymer to introduce polarization defects that destabilize the ferroelectric phase. In another implementation, the electrostrictive relaxor ferroelectric EAP may be formed by irradiating P(VDF-TrFE) with high-energy electrons or protons to cause polarization defects. The electrostrictive relaxor ferroelectric EAP material possess dipoles that may be aligned in a ferroelectric state (beta phase) when an electric field is applied. When the electric field is removed the dipoles return to a paraelectric state (alpha phase). The defects reduce the size of the crystallites which lowers the energy barrier required for transitions between paraelectric and ferroelectric states. The length of the crystallites increase in the ferroelectric state relative to the paraelectric state. In addition, the crystallites in the electrostrictive relaxor ferroelectric EAP layer may be oriented in one direction (e.g., uniaxially). In the uniaxially oriented electrostrictive relaxor ferroelectric EAP the increase length of the crystallites cause a corresponding increase in the EAP material along the orientation direction. In addition, the elastic modulus and the electromechanical strain in the orientation direction can be significantly increased. However, the uniaxially oriented electrostrictive relaxor ferroelectric EAP exhibits minimal electromechanical response in the axis perpendicular to the axis of the orientation direction.

The change in the length of the EAP layers is utilized to control the shape and/or rigidity of the guide wire. The change in the shape and/or rigidity can be used to steer the guide wire along a desired pathway. The change in the shape can also be used to vibrate the guide wire to aid in advancing the guide wire along the desired path. Similarly, the range of rigidity can be used to aid in advancing the guide wire along the desired path. For example, the guide wire may be made relatively flexible to avoid damaging tissue along the path or may be made relatively stiff to push past a particular area.

Electroactive polymers may also be referred to as electromechanical polymers (EMP). The term electroactive polymer as used herein is not intended to be different from electromechanical polymers. Instead, embodiments of the present technology may utilize any electrostrictive relaxor ferroelectric or the like EAP or EMP material.

Figure 3:
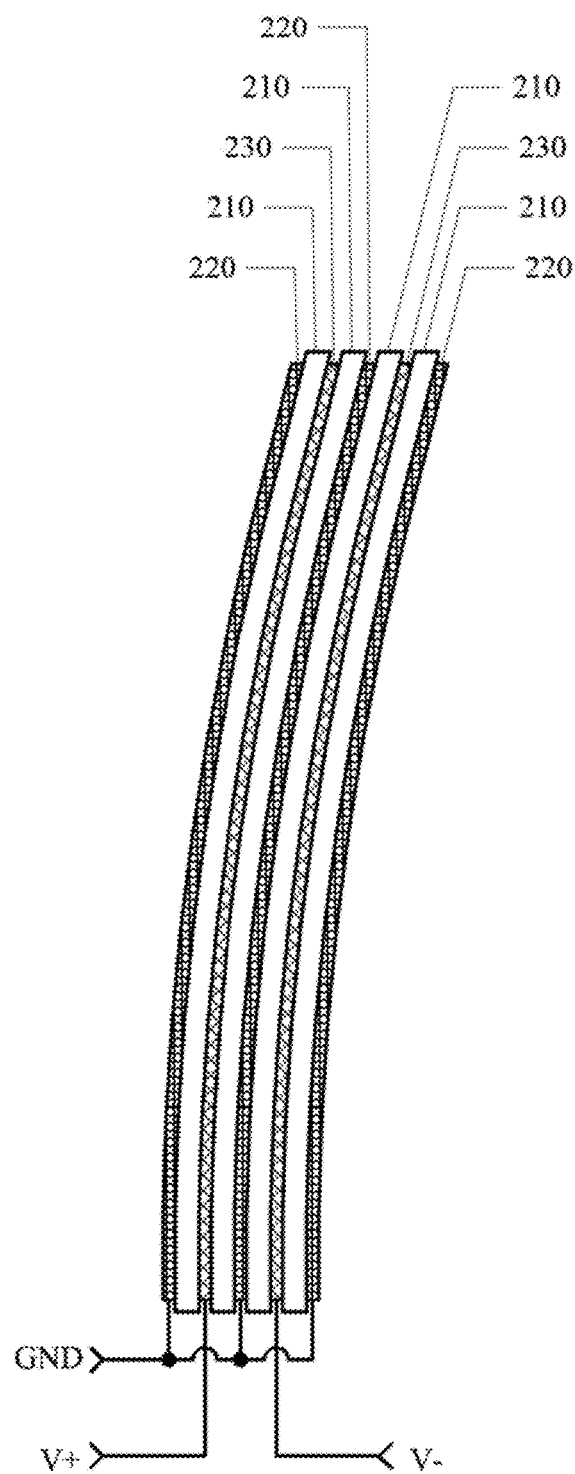
FIG. 3 shows a block diagram illustrating operation of the guide wire medical device, in accordance with one embodiment of the present technology.

Referring now to FIG. 3, operation of the guide wire medical device, in accordance with one embodiment of the present technology, is illustrated. The guide wire may include a plurality of EAP layers, each disposed directly or indirectly between a respective set of a first and second electrode layers. The first and second electrode layers, as illustrated, may be continuous electrode sheets. A potential may be applied across a first set of the plurality of EAP layers causing the first set of EAP layers to expand predominantly in a longitudinal direction. The elongation of the first set of EAP layers relative to the second set of EAP layers causes the guide wire structure to bend in a plane perpendicular to the plane of the layers of the guide wire. The bending can be used to steer the guide wire and/or achieve a particular shape of the guide wire. ID addition, one or more active EAP sections can be placed in tension with one another to achieve a given rigidity.

In one embodiment the EAP layers may be comprised of electrostrictive relaxor ferroelectric EAP material. The electrostrictive relaxor ferroelectric EAP generates a force when biased as a function of the product of the polymer's Young's modulus and the thickness of the polymer when a potential voltage is applied. Therefore, a plurality of EAP layers may be advantageously utilized to increase the force that the guide wire can generate for a given thickness of the EAP layers. Alternatively, a plurality of EAP layers may be advantageously utilizes to reduce the applied potential voltage utilized to generate a given force for a given thickness of the EAP layers.

In an exemplary implementation, the EAP layers may be 3 micro-meters (μm) thick. When an electric potential of 180 V (e.g., 60 V/μm) is applied to the left most EAP layers, for example, the polymer film in such layers becomes longer relative to the other EAP layers, thereby creating a bending motion. In another example, an electric potential of 300 V can be applied to the left most EAP layer while an electric potential of 120 V is applied to the right most EAP layer. The lower potential voltage applied to right most EAP layer resists the bending motion of the left most EAP layer, thereby stiffening the guide wire.

Although FIG. 3 illustrates an embodiment including a plurality of EAP layer, the guide wire may have a single EAP layer. In such case, a single EAP layer coupled to another layer such as a substrate layer, sheath layer, or the like may deflect as a result of the change in length of the EAP layer without a corresponding change in the other layer.

Figure 4:
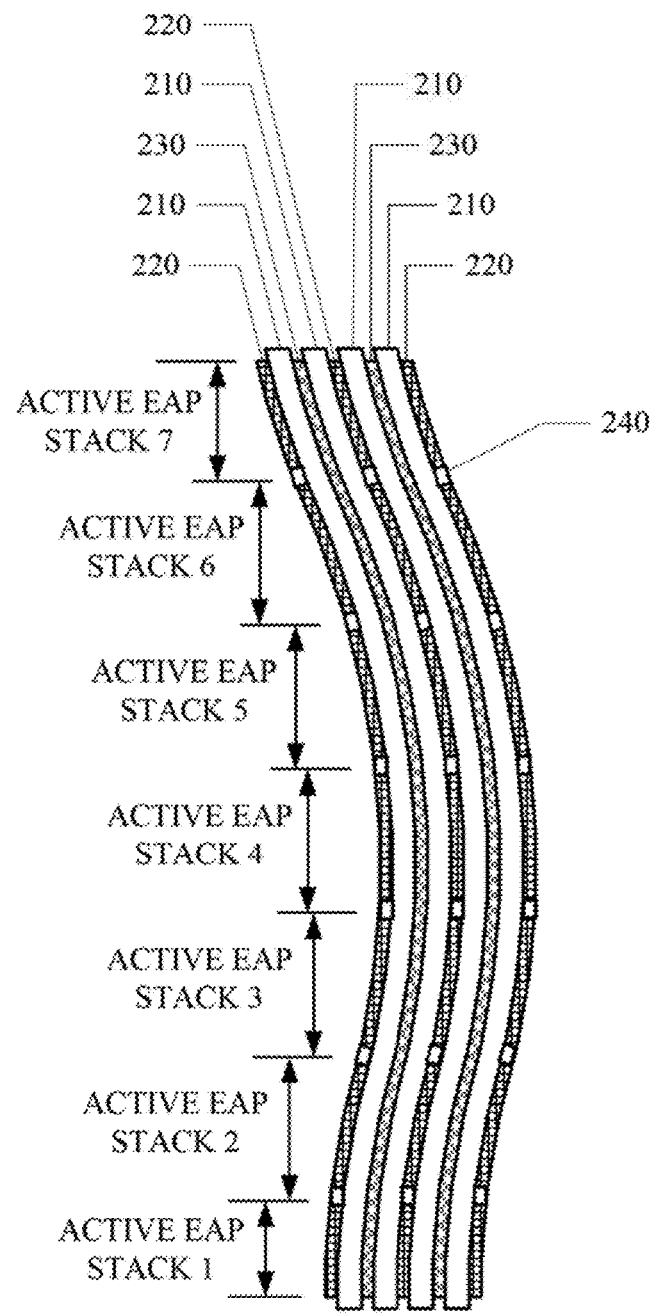
FIG. 4 shows a block diagram illustrating operation of the guide wire medical device, in accordance with another embodiment of the present technology.

Referring now to FIG. 4, operation of the guide wire medical device, in accordance with another embodiment of the present technology, is illustrated. The guide wire may include a plurality of EAP layers, each disposed between a respective set of a first and second electrode layers. Each layer of the first and/or second electrode includes a plurality of electrodes arranged in a given pattern and separated from each other by an insulator region 240. Each electrode in a layer is aligned with the corresponding electrode in the other layers. The portions of the EAP layers disposed between the first and second electrodes are active EAP portions and those portions of the EAP layers that are not disposed between the first and second electrode (e.g., proximate the insulator regions separating electrodes in the same layer) are inactive EAP portions. The active EAP portions are aligned in stacks between the layers of the guide wire.

Different potential voltages can be applied to different electrodes relative to other electrodes in the same layer and/or corresponding electrodes in other layers to form a given shape of the guide wire. For example, a first potential can be applied to the left most active EAP portions in the first active EAP stack to cause a relatively small deflection of the guide wire to the right. A second potential that is larger than the first potential can be applied to the two left most active EAP portion in the second active EAP stack to cause a larger deflection of the guide wire to the right. A third potential can be applied to the right most active EAP in the third active EAP stack to cause the guide wire to reduce the deflection of the guide wire to the right.

Accordingly, the guide wire can advantageously be steered to different places by applying different potential voltages to different active portions of the EAP. Applying different potential voltages to different active portion of the EAP can also be used to change the rigidity of the guide wire or a portion therefore. The applied potential voltages can also be varied to cause the guide wire or a portion thereof to vibrate, which can facilitate advancement of the guide wire along the path.

Figure 5:
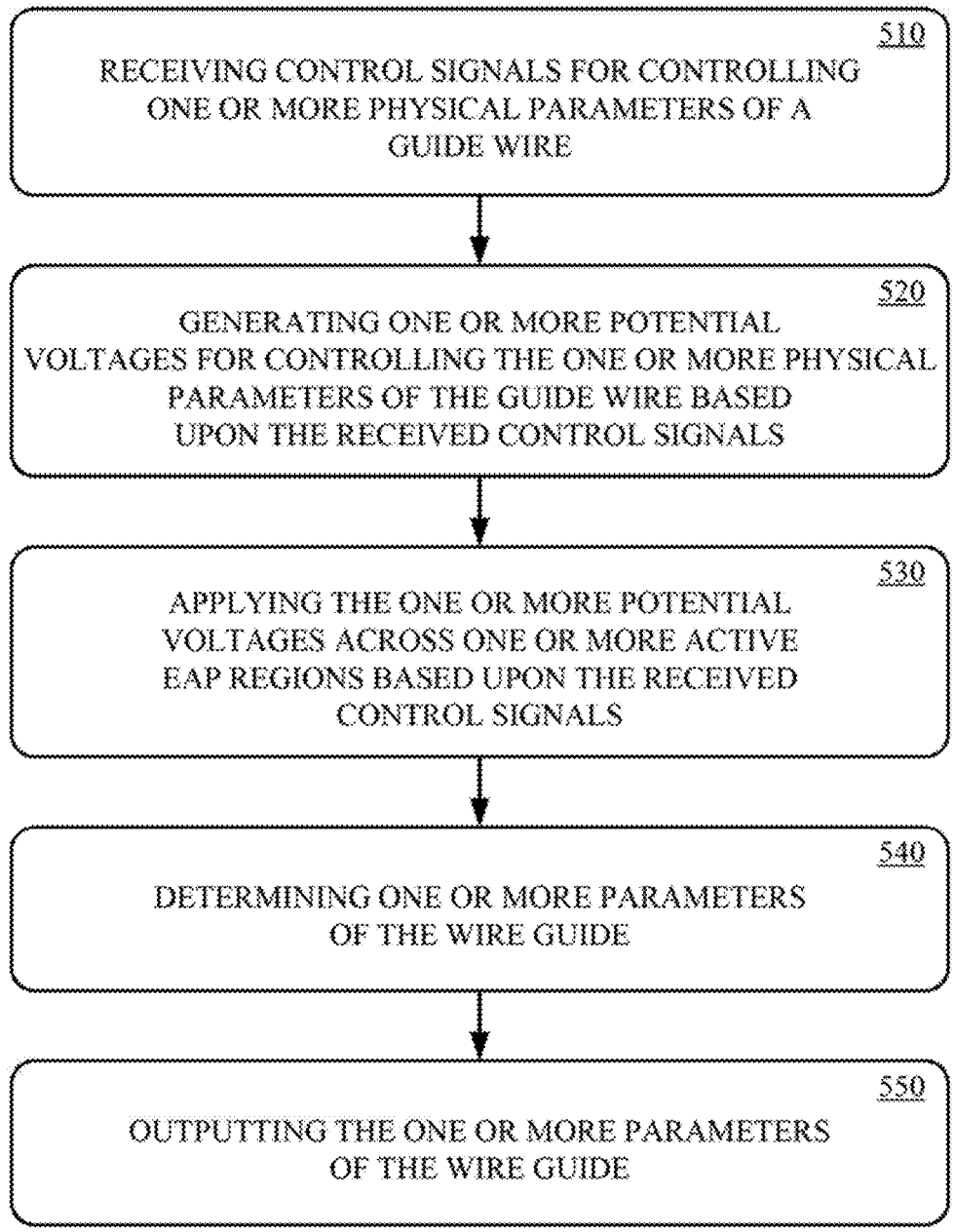
FIG. 5 shows a flow diagram of a method of using a guide wire medical device, in accordance with one embodiment of the present technology.

Referring now to FIG. 5, a method of using the guide wire, in accordance with one embodiment of the present technology, is shown. The method may begin with receiving one or more control signals for controlling one or more physical parameters of the guide wire, at 510. The one or more physical parameters may include the deflection of the guide wire, the rigidity of the guide wire, and/or the like.

At 520, one or more potential voltages are generated for controlling one or more physical parameters of the guide wire based upon the received control signals. At 530, the one or more potential voltages are applied across one or more particular active EAP portions of the guide wire based upon the received, control signals. The potential voltages applied across one or more particular active EAP regions may be adapted to steer the guide wire as it is moved along a pathway within a patient. The applied potential voltages may also be adapted to form and/or hold a particular shape in the guide wire alone or in combination with steering the guide wire. The applied potential voltages may also be adapted to control the rigidity from relatively flexible to relatively rigid. The applied potential voltages may also be adapted to vibrate one or more portions of the guide wire.

At 540, one or more parameters of the guide wire may be determined. In one implementation, the insertion depth of the guide wire, the deflection of the guide wire, or the like is determined from one or more gauges. The one or more determined parameters of the guide wire may be output, at 550. In one embodiment, the one or more determined parameter of the guide wire may be output for use in generating additional control signals for controlling the one or more physical parameter of the guide wire, presentation on a display an operator of the guide wire, and/or the like.

Figure 6:
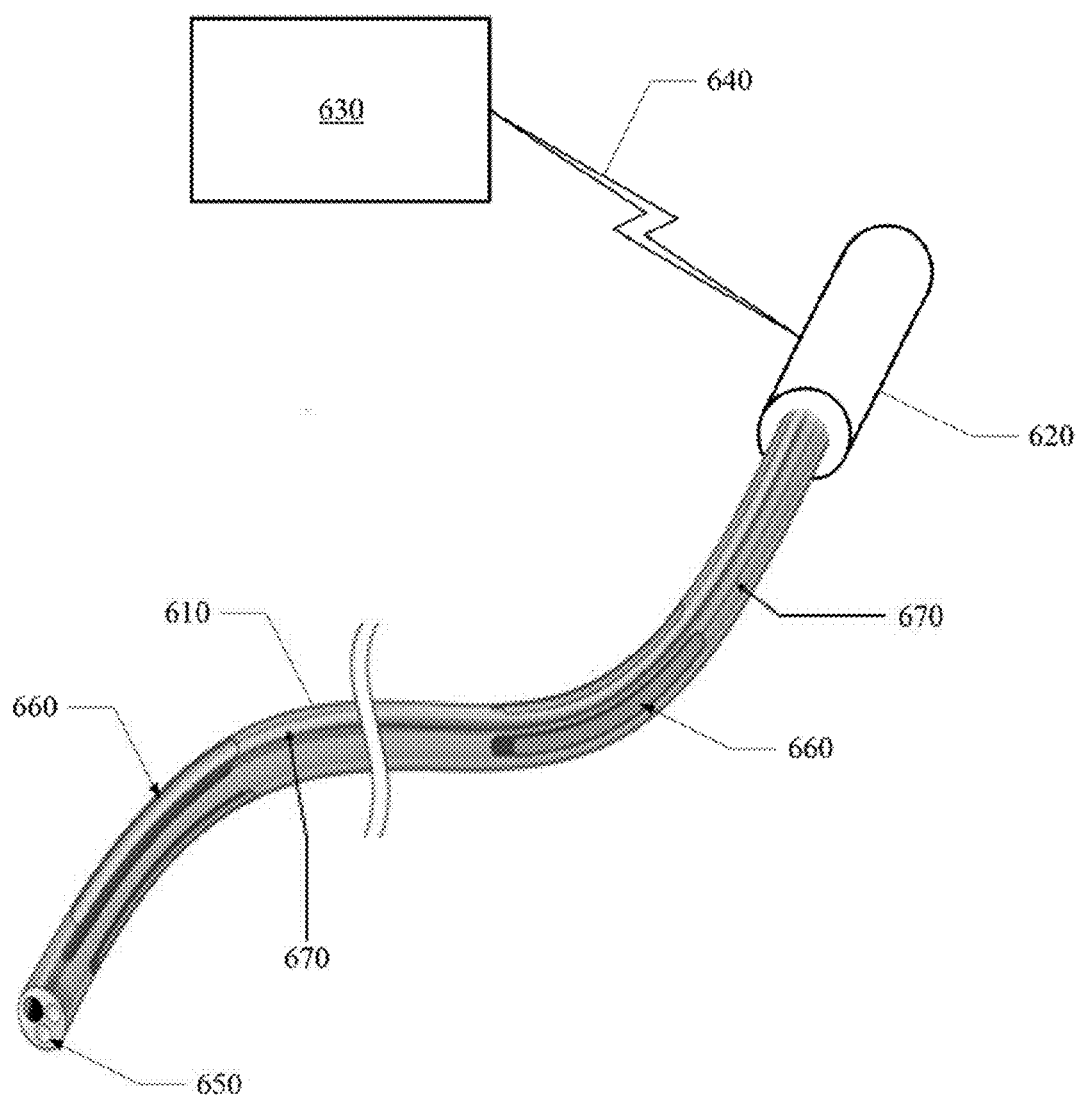
FIG. 6 shows a block diagram of an exemplary guide wire medical system, in accordance with one embodiment of the present technology.

Referring now to FIG. 6, an exemplary medical system, in accordance with one embodiment of the present technology, is shown. In one implementation, the system includes a guide wire or catheter 610, a drive unit 620 coupled to the guide wire or catheter, and a control system 630 communicatively coupled 640 to the drive unit. The control system may be communicatively coupled to the drive unit by one or more wired and/or wireless communication links.

The guide wire or catheter 610 may include one or more lumens 650, such as a lumen for passing a liquid for flushing the body lumen, a lumen for a camera, a lumen for a device such as an ablation tip, and/or the like. A plurality of multi-layer EAP actuators 660 may be molded into a body lumen material, or the guide wire or catheter may be substantially formed by the multi-layer EAP actuators as illustrated in other embodiments herein. The multi-layer EAP actuators 660 may be arranged in one or more sets. The multi-layer EAP actuators 660 are couple to the drive unit by respective electrical interconnects 670.

Figure 7:
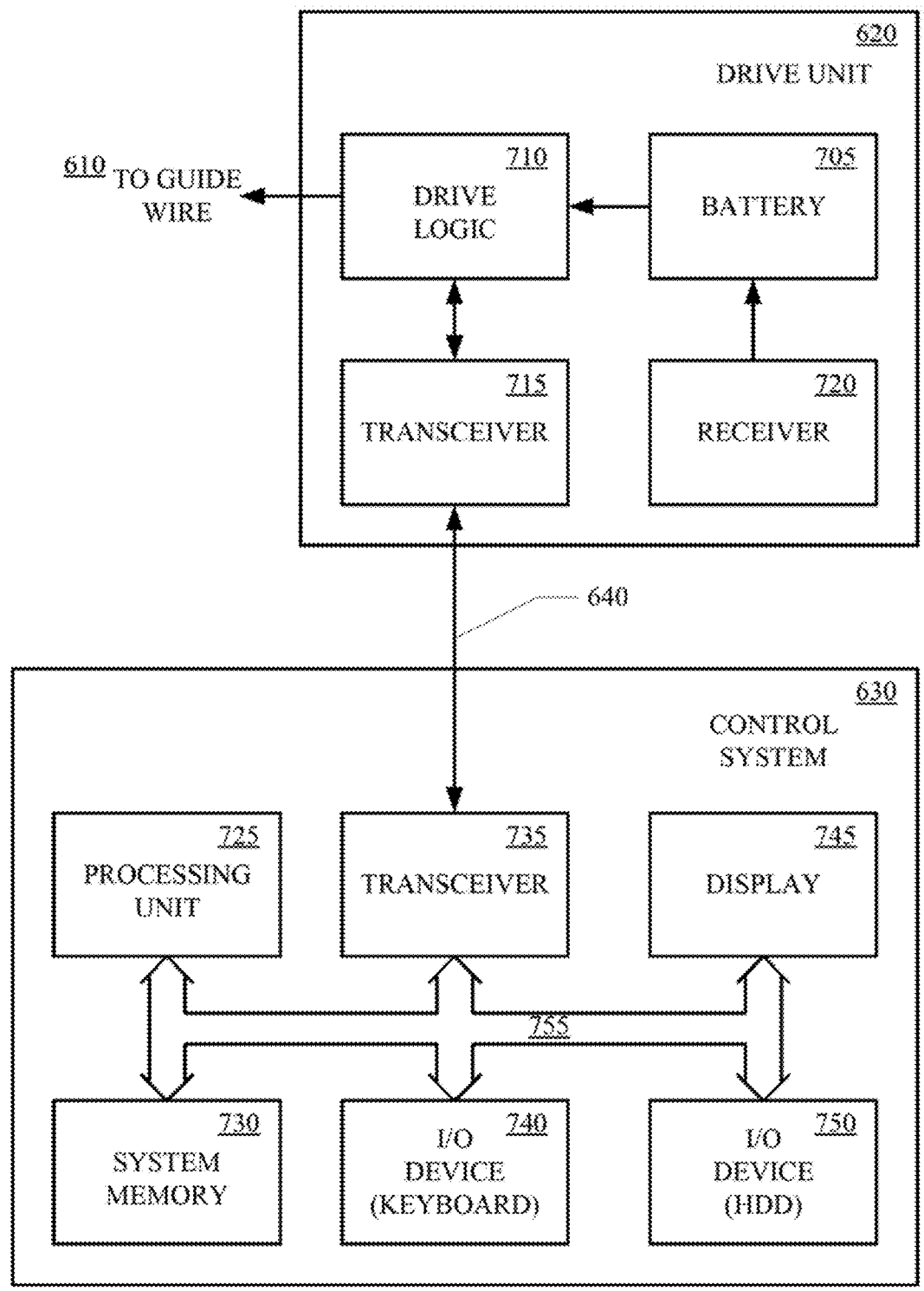
FIG. 7 shows a block diagram of a guide wire drive unit and control system, in accordance with one embodiment of the present technology.

Referring now to FIG. 7, an exemplary drive unit 620 and exemplary control system 630, in accordance with embodiments of the present technology is shown. The drive unit 620 may include a power source 705, drive logic 710 and a transceiver 715. The drive logic, is coupled to the power source and the transceiver. The power source may be a battery in one implementation. In an exemplary implementation, the power source may be a rechargeable battery. The battery may be wirelessly recharged from electromagnetic energy received through an optional wireless recharge receiver 720 coupled to the rechargeable battery. In another implementation, the power source is provided by the control system or another device.

The control system may be a dedicated system or may a general purpose computing system, such as a personal computer (PC), workstation, or the like. The control system 530 may include a processing unit 725, system memory 730, a transceiver 735, and one or more additional input/output devices 740-750 communicatively coupled together by one or more buses 755. The input/output device may include a keyboard 740, a pointing device, a display 745, a hard disk drive (HDD) 750 an optical disk drive, and/or the like. The system memory (e.g., computing device readable media) is adapted to store instructions (e.g., computing device executable instructions) and data which when executed by the processing unit perform one or more processes for controlling the guide wire.

In particular, the processing unit generates control signals for controlling one or more physical parameter of the guide wire. The transceiver of the control system is adapted to send the control signals to the transceiver of the drive unit. The drive logic generates one or more potential voltages from the power source in accordance with the received control signals. The drive logic applies the one or more potential voltages across one or more active EAP regions based upon the received control signals. The applied voltage potentials may steer the tip of the guide wire, change the shape of the guide wire, change the rigidity of the guide wire and/or cause the guide wire to vibrate.

The transceiver of the drive unit may also be adapted to provide control signals regarding one or more parameters of the guide wire to the guide wire control system. For example, one or more strain gauges (not shown) in the guide wire may generate location control signals that are received by the transceiver of the control system and output on a display.

The control signals may be generated as a function one or more predetermined software routines (e.g., preconfigured), as a function of guide wire position and pathway information from another device (e.g., automatic), as a function of operator input (e.g., manual), and/or the like. The generated control signals may steer the lead section of the guide wire and control the following sections to have the deflection of the lead section when it was present at the corresponding depth. The generated control signals may change the rigidity of the guide wire and/or cause the guide wire to vibrate. The functions of steering, shaping, controlling the rigidity and/or vibrating the guide wire may advantageously reduce trauma to the surrounding tissue.

Again, embodiments of the present technology, such as the method of use described in FIG. 5, the medical system described in FIG. 6 and the drive unit described in FIG. 7, may be applied to other medical devices such as catheters or the like percutaneous instruments.

Figure 8:
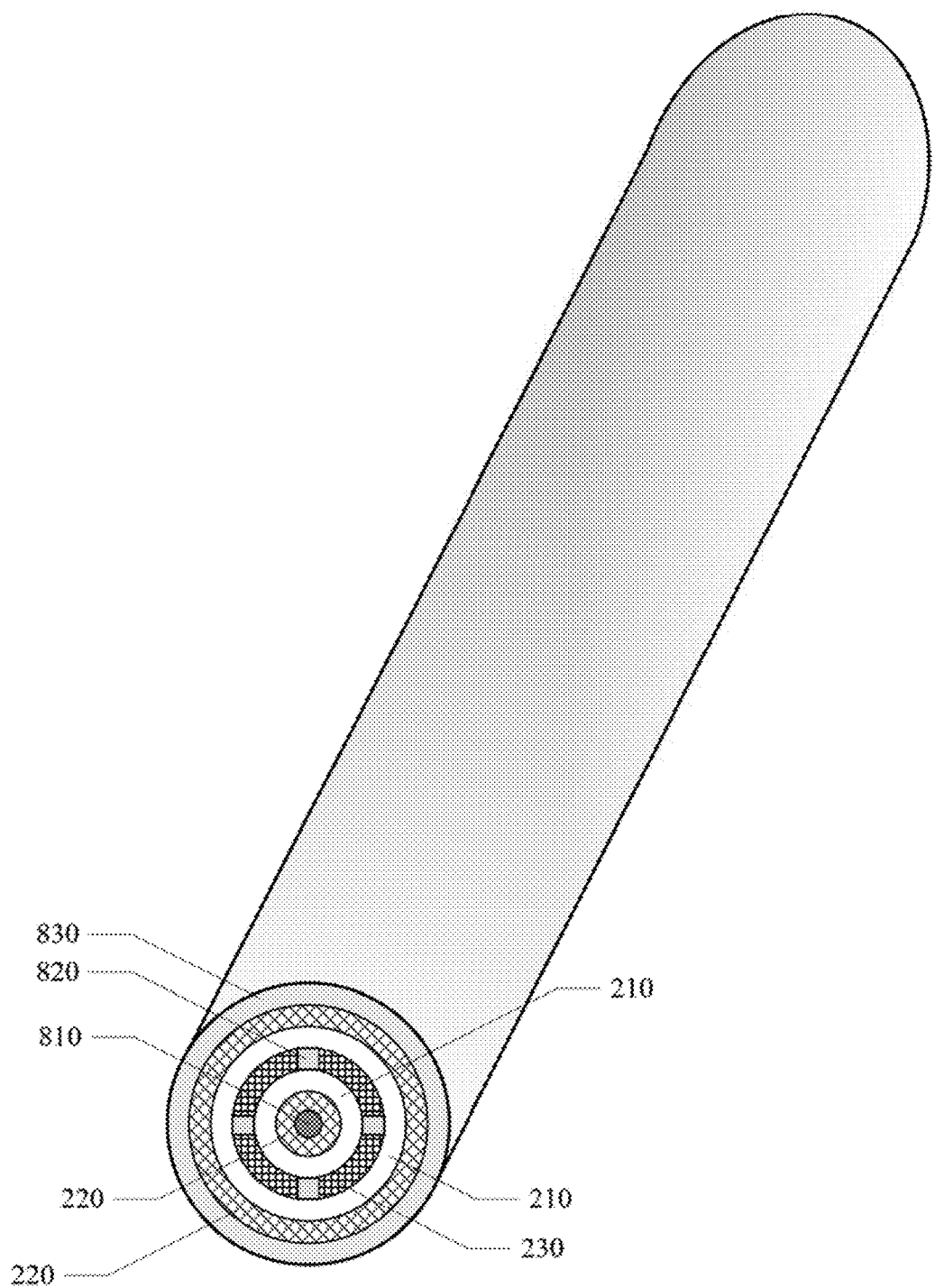
FIG. 8 shows a block diagram of a guide wire medical device, in accordance with another embodiment of the present technology.

Referring now to FIG. 8, a guide wire medical device, in accordance with another embodiment of the present technology, is shown. The guide wire may include a core 810, one or more EAP layers 210, one or more layers of a first electrode 220 and one or more layers of a second electrode 230. The one or more EAP layers are disposed between alternating ones of the first electrode and second electrode. The stack of one or more EAP layers and alternating first and second electrodes may be disposed around a portion of the core or the entire length of the core. The guide wire may further include one or more insulator layers 820, electrical interconnect layers, sheath layers 830, and the like. The guide wire may further include additional layers for forming strain gauges, temperature sensors, heating elements, cooling elements, and/or the like. In another embodiment, the first or second electrode or a portion thereof may be the core of the guide wire.

Figure 9:
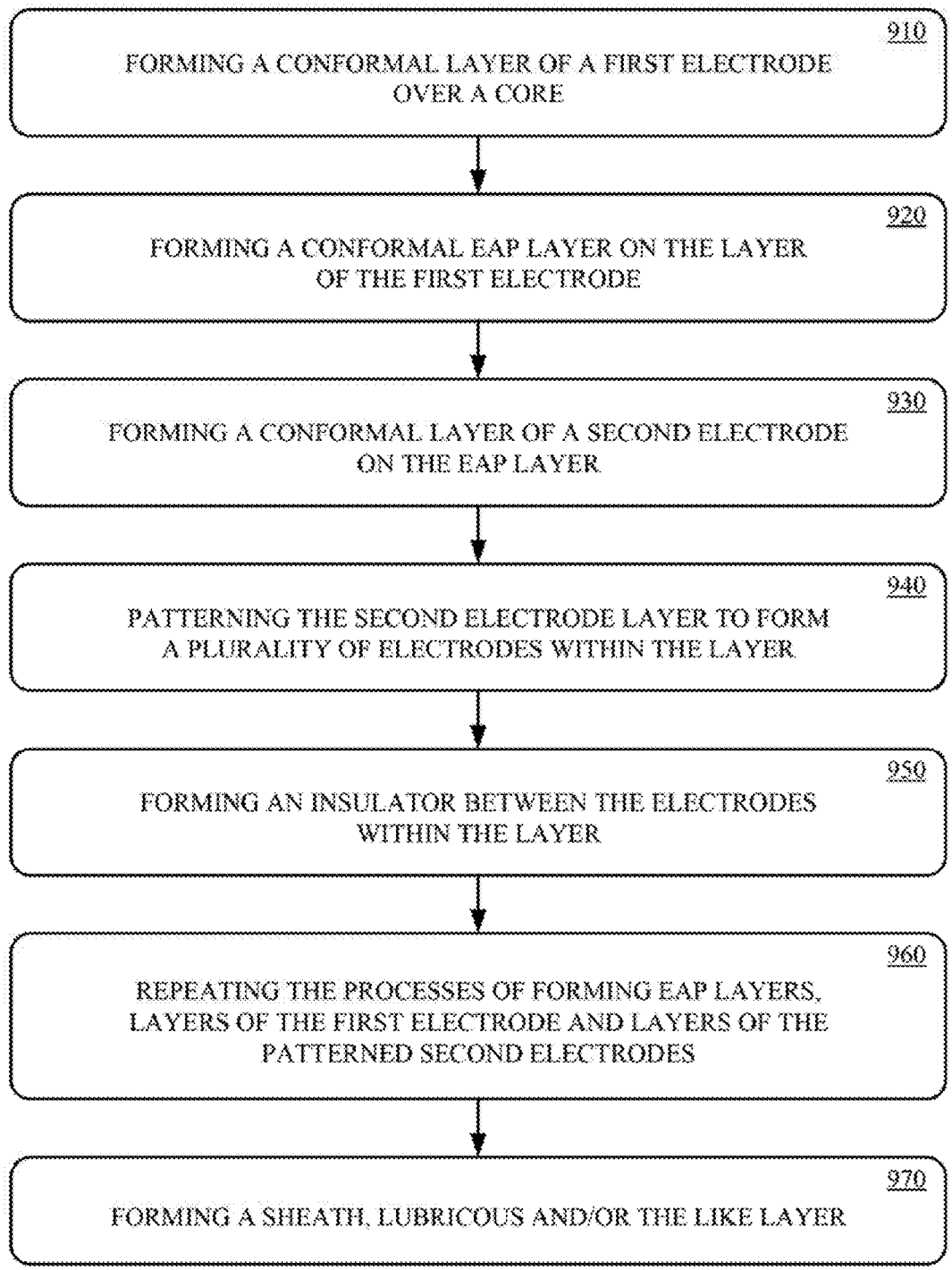
FIG. 9 shows a flow diagram of a method of manufacturing a guide wire medical device, in accordance with one embodiment of the present technology.

Referring now to FIG. 9, a method of manufacturing the guide wire illustrated in FIG. 8, in accordance with one embodiment of the present technology, is shown. The process may include forming a layer of a first electrode over a core, at 910. The core may be a nitinol (e.g., alloy of nickel and titanium), plastic, or the like wire that resist kinking. The first electrode may be formed directly on the core or on an optional intervening insulator layer. The first electrode layer may be formed by dip or spray coating, sputtering, platting, vapor deposition or the like of a conductive material conformally onto the core. In one implementation, the first electrode layer may be formed by sputtering gold, titanium, aluminum or the like on the core or an intervening insulator layer. Alternatively, the core if conductive may be utilized as the first electrode.

At 920, an EAP layer is formed on the layer of the first electrode. The EAP layer may be formed by dip or spray coating, sputtering, vapor deposition or the like of an EAP material conformally onto the first electrode layer. In one implementation, the EAP layer is prepared and synthesized by ploymerizing processes such as suspension, emulsion or solution methods. The monomers (e.g., VDF, TrFE, CFE) are selected and contacted or mixed in proportion in the presence of a suitable catalyst or initiator. The resulting polymer system should have a convenient molecular weight suitable for use in an electrical or electromechanical device. The molecular weight of the polymer system is, however, not limited. The molecular weight of polymer is preferably, but not limited, to higher than about 50,000, 100,000 or 300,000.

In one embodiment, the EAP material may be an electrostrictive relaxor ferroelectric EAP. In one implementation, the electrostrictive relaxor ferroelectric EAP may be formed from a ferroelectric polymer by introducing crystallinity reducing monomers such as chlorofluoroethylene (CFE) and chlorotrifluoroethylene (CTFE) or hexafluoropropylene to the copolymer. The electrostrictive relaxor ferroelectric EAP material may include at least one monomer of vinylidenefluoride, at least one monomer selected from the group consisting of trifluoroethylene and tetrafluoroethylene, and at least one monomer selected from the group consisting of tetrafluoroethylene, vinyl fluoride, perfluoro (methyl vinyl ether), bromotrifluorethylene, chlorofluoroethylene, chlorotrifluoroethylene, and hexafluoropropylene. Exemplary terpolymers may be a polyvinylidene fluoride (PVDF) such as $P(VDF_x\text{-}TrFE_y\text{-}CFE_{1-x-y})$, $P(VDF_x\text{-}TrFE_y\text{-}CTFE_{1-x-y})$, poly $(VDF_x\text{-}TrFE_y\text{-}vinylidene\ chloride_{1-x-y})$, poly(vinylidene fluoride-tetrafluoroethylene-chlorotrifluoroethylene), poly (vinylidene fluoride-trifluoroethylene-hexafluoropropylene), poly(vinylidene fluoride-tetrafluoroethylene-hexafluoropropylene), poly(vinylidene fluoride-trifluoroethylene-tetrafluoroethylene), poly(vinylidene fluoride-trifluoroethylene-vinyl fluoride), poly(vinylidene fluoride-tetrafluoroethylene-vinyl fluoride), poly(vinylidene fluoride-trifluoroethylene-perfluoro(methyl vinyl ether)), poly (vinylidene fluoride-tetrafluoroethylene-perfluoro (methyl vinyl ether)), poly(vinylidene fluoride-trifluoroethylene-bromo trifluoroethylene, polyvinylidene), poly(vinylidene fluoride-tetrafluoroethylene-chlorofluoroethylene), poly(vinylidene fluoride-trifluoroethylene-vinylidene chloride), and poly(vinylidene fluoride-tetrafluoroethylene-vinylidene chloride), and wherein x is in the range from 0.5 to 0.75, and y is in the range 0.45 to 0.2 and x+y is less than 1. In another implementation, the electrostrictive relaxor ferroelectric EAP may be formed by irradiating a polyvinylidine fluoride polymer, such as polyvinylidine fluoride-trifluoroethylene P(VDF-TrFE), polyvinylidine fluoride tetrafluoroethylene P(VDF-TFE), polyvinylidine fluoride trifluoroethylene-hexafluoropropylene P(VDF-TFE-HFE) and polyvinylidine fluoride-hexafluoropropylene P(VDF-HFE) with high-energy electrons or protons. The EAP may then be irradiated in an oxygen free atmosphere with an electron energy in the range from about 500 kilo-electron volts (Key) to about 3 mega-electron volts. MeV) to produce the electrostrictive relaxor ferroelectric EAP At 930, a layer of a second electrode, is formed on the EAP layer. The second electrode layer may be formed by dip or spray coating, sputtering, platting, vapor deposition or the like of a conductive material conformally onto the EAP layer. At 940, the second electrode layer is patterned to form a plurality of electrodes within the layer. At 950, an insulator is formed between the electrodes. In one implementation, an insulator material may be conformity coated, sputter, vapor deposited or the like into and between the patterned electrodes of the second electrode layer. The insulator material is then etched back until only the insulator material between the patterned electrodes remains.

Alternatively, an insulator layer may be formed on the EAP layer. The insulator layer may be formed by dip or spray coating or vapor deposition of an insulator onto the EAP layer. The insulator layer is patterned to form inter-electrode insulator regions. In one implementation, the insulator layer may be patterned utilizing one or more electrode masks. A layer of a plurality of second electrodes is formed between the inter-electrode insulator regions. The layer of the second electrodes may be formed by sputtering, platting or the like. One or more electrode masks may also be used to control the deposition of the second electrode material to form a plurality of electrodes between the inter-electrode insulator regions.

At 960, the processes of forming EAP layers, layers of the first electrode and layers of the second electrodes may be repeated any number of times to form a plurality of EAP layers each disposed between a layer of a first electrode and a layer of second electrodes, wherein the patterning of plurality of the second electrodes in each respective layer are aligned with the patterning of the second electrodes in the other respective layers. For example, another EAP layer may be formed on the layer of the second electrodes. The EAP layer may again be formed by dip or spray coating, sputtering, vapor deposition or the like. Another layer of the first electrode may then be formed on the EAP layer. The additional layer of the first electrode may again be formed by dip or spray coating, sputtering, platting, vapor deposition or the like of a conductive material. The processes of thrilling additional EAP layers, additional layers of the first electrode and additional layers of the second electrodes may be repeated any number of times to form concentric active EAP regions. The concentric active EAP regions are radial aligned with each other along the axis of the guide wire to forms radial stacks of active EAP regions.

The process may conclude with forming a sheath layer, lubricous layer, and/or the like, at 970. The layer may be formed by dip or spray coating, sputtering, vapor deposition of the like of a polymer and/or lubricous material. The lubricous material may be fluoropolymer, hydrophilic coating, urethane or other materials known to those experienced in the field.

Figure 10:
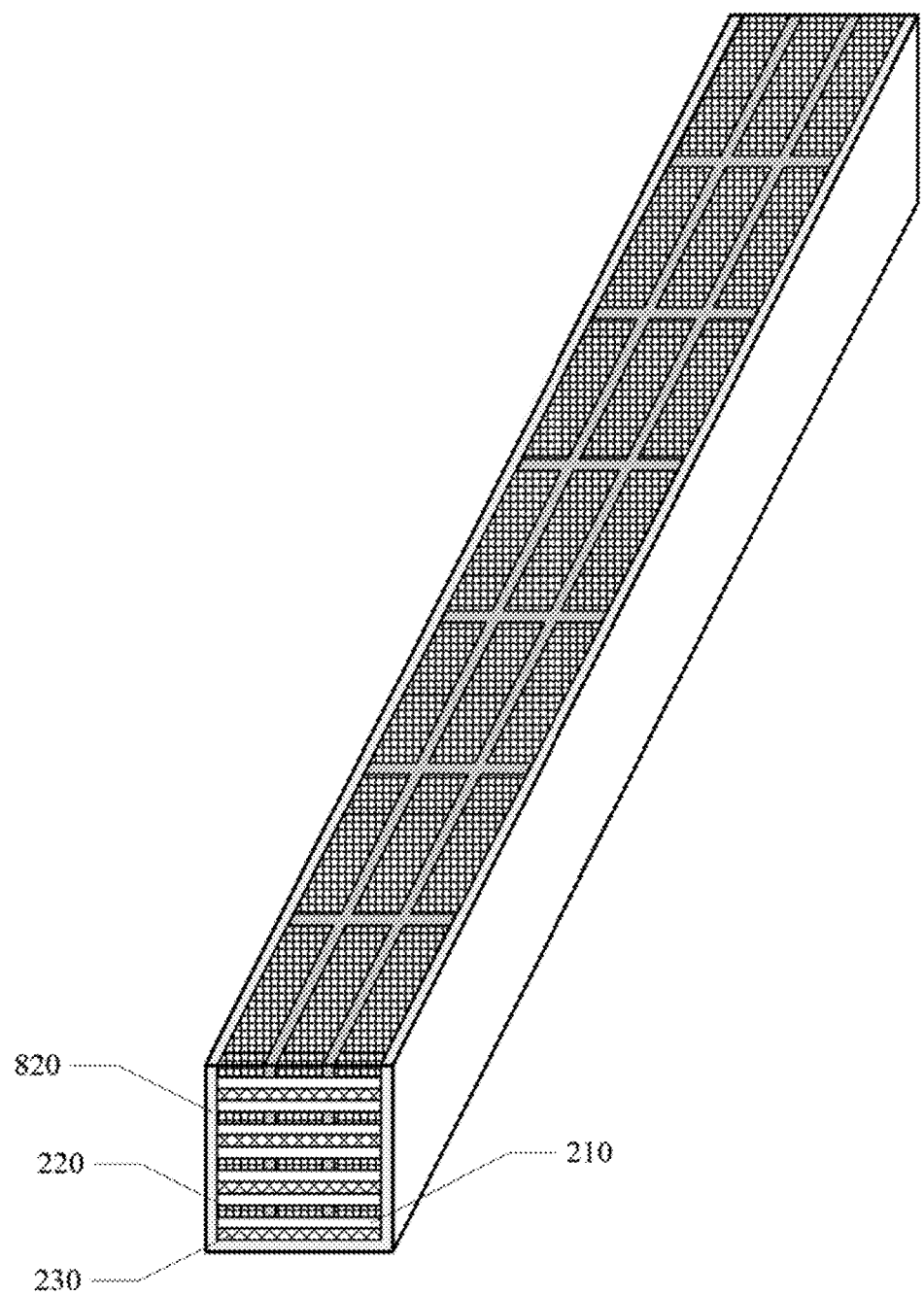
FIG. 10 shows a block diagram of a guide wire medical device, in accordance with another embodiment of the present technology.

Referring now to FIG. 10, a guide wire, in accordance with another embodiment of the present technology, is shown. The guide wire may include one or more EAP layers 210, one or more layers of a first electrode 220 and one or more layers of a second electrode 230. The guide wire may also include one or more insulator layers 820, electrical interconnect layers, sheath layers, and the like. The guide wire may further include additional layers (not shown) for forming strain gauges, temperature sensors, heating elements, cooling elements, variable or single frequency vibrating elements and/or the like.

Figure 11:
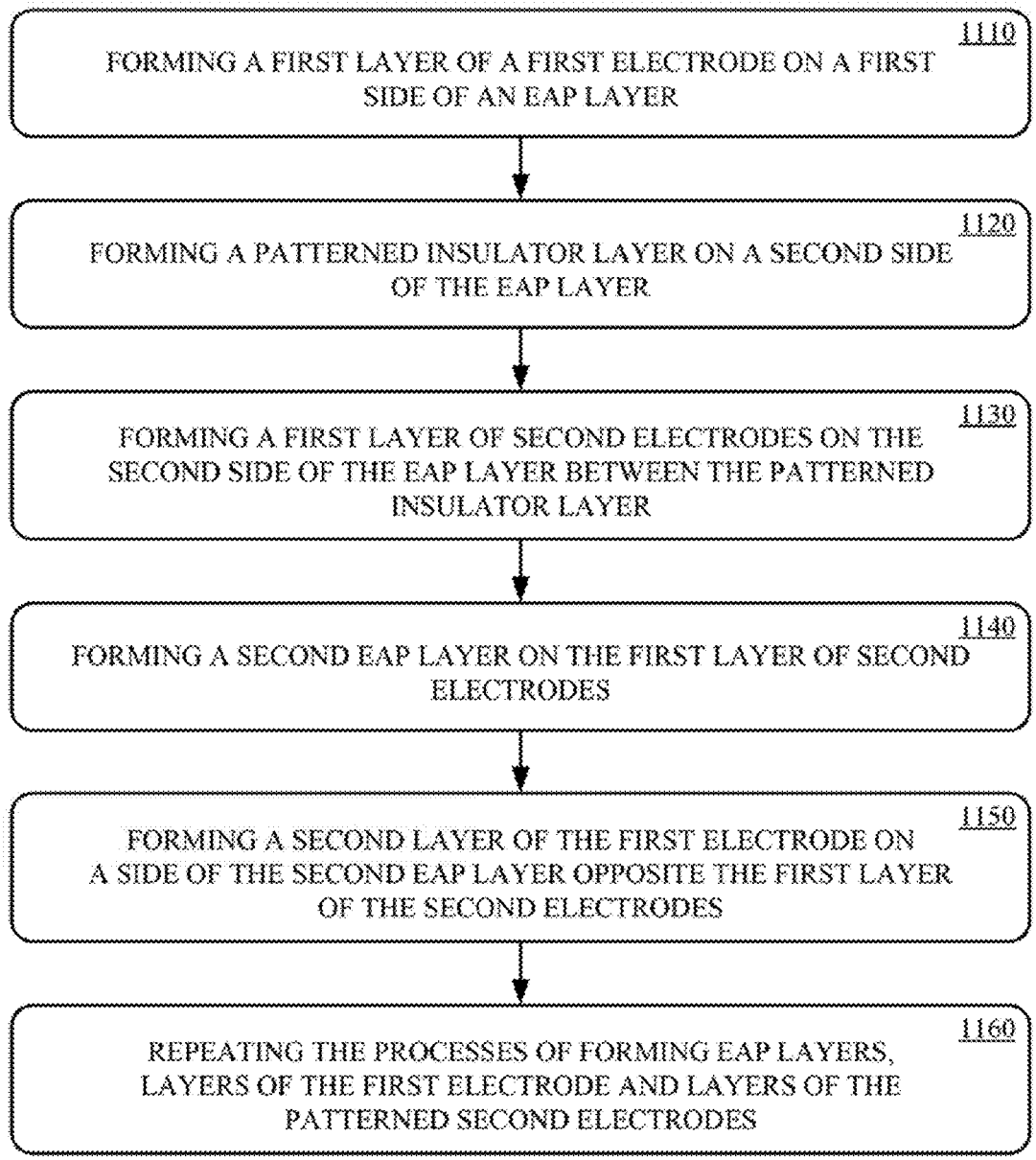
FIG. 11 shows a flow diagram of a method of manufacturing a guide wire medical device, in accordance with another embodiment of the present technology.

Referring now to FIG. 11, a method of manufacturing the guide wire illustrated in FIG. 10, in accordance with one embodiment of the present technology, is shown. The process may include forming a first layer of a first electrode on a first side of a first EAP layer, at 1110. In one implementation, the EAP layer is prepared and synthesized by polymerizing processes such as suspension, emulsion or solution methods. The resulting polymer system should have a suitable molecular weight for application in the device.

Again, the EAP material may, in one embodiment, be an electrostrictive relaxor ferroelectric EAP. In one implementation, the electrostrictive relaxor ferroelectric EAP may be formed from a ferroelectric polymer by introducing chloride containing monomers such as chlorofluoroethylene (CFE) and chlorotrifluoroethylene (CTFE) or hexafluoropropylene to the copolymer. In another implementation, the electrostrictive relaxor ferroelectric EAP may be formed by irradiating a polyvinylidine fluoride polymer.

At 1120, a patterned insulator layer may be formed on a second side of the EAP layer. In one implementation, the insulator layer may be formed by vapor deposition of insulator onto the EAP layer. The insulator layer is patterned utilizing one or more electrode mask layers. At 1130, a first layer of second electrodes is formed on the second side of the EAP layer between the patterned insulator layer. The second electrode layer may be formed by sputtering, platting or the like a conductive material, such as gold, titanium, or aluminum, onto the EAP layer exposed by the patterned insulator layer.

At 1140, a second EAP layer is formed on the first layer of second electrodes. At 1150, a second layer of the first electrode is formed on a side of the second EAP layer opposite the first layer of the second electrodes.

At 1160, the processes of forming EAP layers, and alternating layers of the first electrode and layers of the second electrodes are repeated any number of times to form a plurality of EAP layers each disposed between a layer of a first electrode and a layer of second electrodes, wherein the patterning of plurality of the second electrodes in each respective layer are aligned with the patterning of the second electrodes in the other respective layers. Furthermore, the EAP layers and layers of first elector and second electrodes may be manufacture in sheet form containing a plurality of individual guide wires. In such case the sheets may be cut to separate the plurality of individual guide wires.

The process may conclude with forming a sheath layer, lubricous layer, and/or the like. The layer may be formed by dip or spray coating, sputtering, vapor deposition of the like of an insulator and/or lubricous material. The lubricous material may be fluoropolymer, hydrophilic coating, urethane or other materials known to those experienced in the field.

Figure 12:
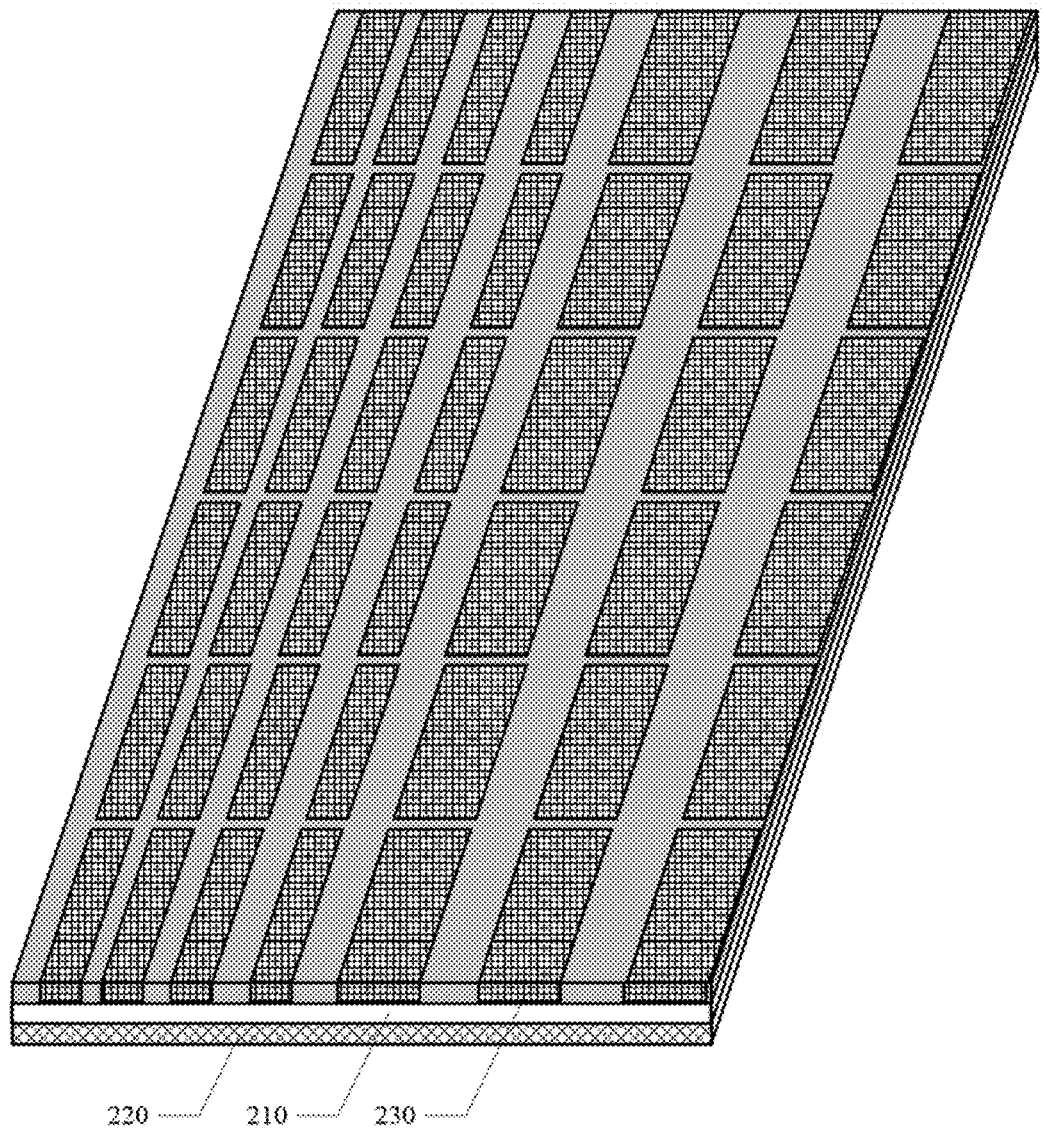
FIG. 12 shows a block diagram of a guide wire medical device, in accordance with yet another embodiment of the present technology.

Referring now to FIG. 12, a partially fabricated guide wire, in accordance with another embodiment of the present technology, is shown. A sheet used to form the guide wire may include an EAP layer 210, a first electrode layer 220 and a layer of a plurality of second electrodes 230. The plurality of second electrodes are arranged in a pattern such that when the sheet is rolled, folded or the like, corresponding second electrodes are aligned to form a stack of active EAP regions. The sheet may be rolled, folded or the like about itself one or more times to form stacked of two or more active EAP regions. In another implementation, a plurality of sheets may be rolled, folded or the like, together to form the guide wire. The guide wire may further include one or more insulator layers, electrical interconnect layers, sheath layers, and the like. The guide wire may further include additional layers (not shown) for forming strain gauges, temperature sensors, heating elements, cooling elements, variable or single frequency vibrating elements and/or the like.

Figure 13:
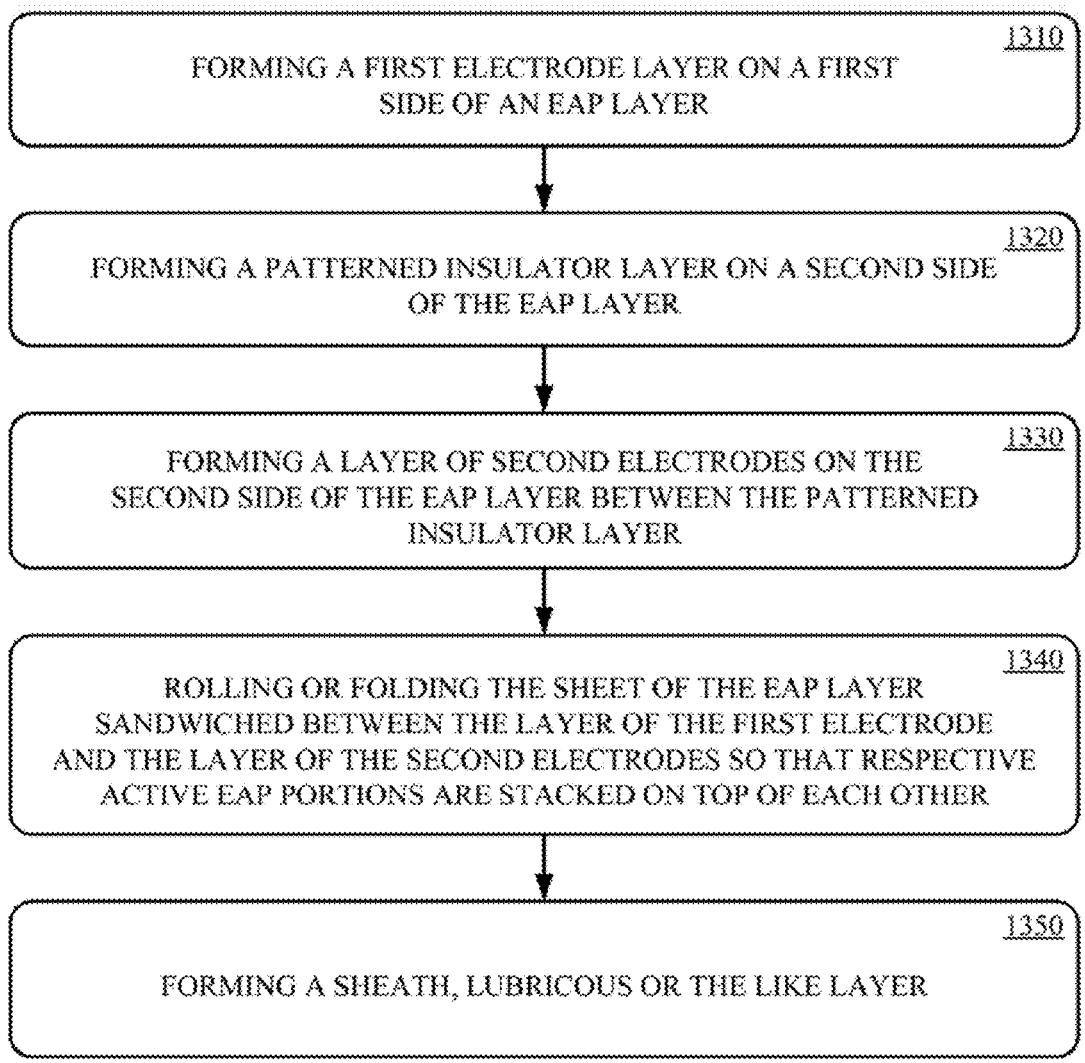
FIG. 13 shows a flow diagram of a method of manufacturing a guide wire medical device, in accordance with yet another embodiment of the present technology.

Referring now to FIG. 13, a method of manufacturing the guide wire illustrated in FIG. 12, in accordance with one embodiment of the present technology, is shown. The process may include forming a layer of a first electrode on a first side of an EAP layer, at 1310. In one implementation, the EAP layer is prepared and synthesized by polymerizing processes such as suspension, emulsion or solution methods. The resulting polymer system should have a suitable molecular weight for application in the device. Again, the EAP material may, in one embodiment, be an electrostrictive relaxor ferroelectric EAP. In one implementation, the electrostrictive relaxor ferroelectric EAP may be formed from a ferroelectric polymer by introducing defects that shorten the crystallites of the polymer material.

At 1320, a patterned insulator layer may be formed on a second side of the EAP layer. In one implementation, the insulator layer may be formed by vapor deposition of insulator onto the EAP layer. The insulator layer may then be patterned utilizing one or more electrode mask layers. The mask layers may have a geometric pattern that expands in the direction that the sheet will be rolled, folded or the like. At 1330, a layer of second electrodes is formed on the second side of the EAP layer between the patterned insulator layer. The layer of second electrodes may be formed by sputtering a conductive material, such as gold, aluminum or titanium, onto the HAP layer exposed by the patterned insulator layer.

At 1340, the sheet of the EAP layer sandwiched between the layer of the first electrode and the layer of the second electrodes is then roiled, folded or the like such that respective active HAP portions are stacked on top of each other. The process may conclude with forming a sheath layer, lubricous layer, and/or the like, at 1350. The layer may be formed by dip or spray coating, sputtering, vapor deposition of the like of an insulator and/or lubricous material. The lubricous material may be a fluoropolymer, hydrophilic coating, urethane or other materials known to those experienced in the field.

Alternatively, the sheet described in FIGS. 12 and 13 may be utilized to form a catheter by rolling or folding the sheet such that the sheet is formed about a lumen, duct, channel, tube, pipe or the like (hereinafter simply referred to as a catheter lumen). Furthermore, the plurality of second electrodes are arranged such that corresponding second electrodes are aligned to form a stack of active HAP regions about the catheter lumen.

Figure 14:
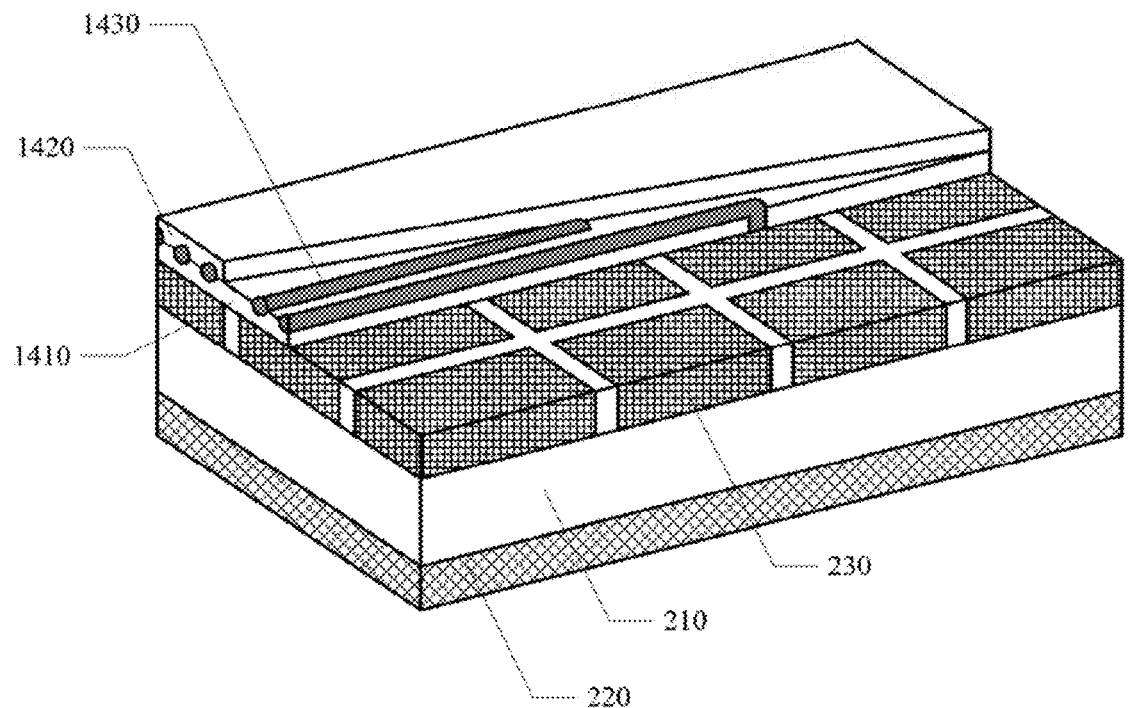
FIG. 14 shows a block diagram of a guide wire medical device, in accordance with another embodiment of the present technology.

Referring now to FIG. 14, a portion of a sheet used to form a guide wire, in accordance with another embodiment of the present technology, is shown. The sheet, of which only a portion is illustrated in the figure, may for example be rolled or folded to form a guide wire, catheter or similar medical device. The guide wire may include one or more EAP layers 210, one or more layers of a first electrode 220, one or more layers of a second electrode 230, one or more insulator layers 1410, 1420, one or more electrical interconnect layers 1430, sheath layers, and the like. The guide wire may further include additional layers (not shown) for forming, strain gauges, temperature sensors, heating elements, cooling elements, variable frequency vibration and/or the like.

For example, the guide wire includes a first EAP layer disposed between a first electrode, and a plurality of second electrodes. The first electrode is coupled by one or more electrical interconnects not shown) to a drive unit. A first insulator layer may be disposed on the plurality of second electrodes. Each of a plurality of interconnects is coupled to a respective one of the plurality of second electrodes through the first insulator layer. A second insulator layer may be disposed over the first insulator layer and the plurality of interconnects to encapsulate the plurality of interconnects. The interconnects each couple a respective one of the plurality of second electrodes to the drive unit.

The insulator regions may be formed by vapor deposition of an insulator material. The insulator regions may in some cases be EAP when not disposed between a first and second electrode. The plurality of interconnects may be formed by sputtering, platting and/or the like gold, titanium, aluminum and/or the like on the first insulator layer to form a conductive film, forming an interconnect mask and etching the conductive film exposed by the mask.

Figure 15:
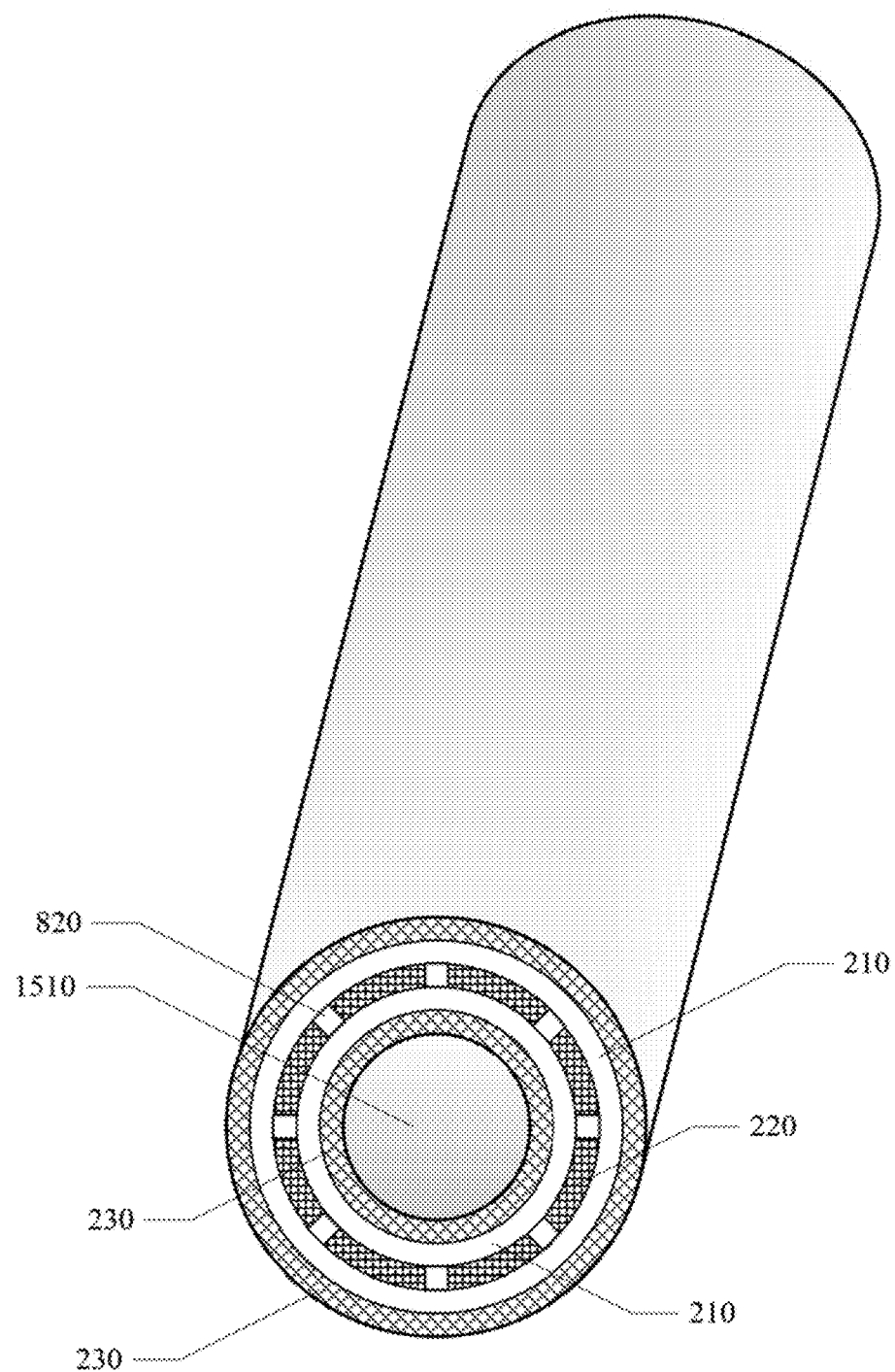
FIG. 15 shows a block diagram of a catheter medical device, in accordance with yet another embodiment of the present technology.

Referring now to FIG. 15, a catheter medical device, in accordance with another embodiment of the present technology, is shown. The catheter may include one or more layers of an EAP material 210, one or more layers of a first electrode 220 and one or more layers of a second electrode 230. The one or more EAP layers are disposed between alternating ones of the first electrode and second electrode. The catheter may further include one or more insulator layers, electrical interconnect layers, sheath layers, and the like. The catheter may further include additional layers for forming strain gauges, temperature sensors, heating elements, cooling elements variable frequency vibration and/or the like.

In one embodiment, a layer of a first electrode is formed on a first side of an EAP layer. The EAP layer, in one implementation, may be a sheet of electrostrictive relaxor ferroelectric EAP material. A patterned insulator layer 820 may be formed on a second side of the EAP layer. A layer of second electrodes is formed on the second side of the EAP layer between the patterned insulator layer. The second electrodes formed on the EAP exposed by the patterned insulator layer are therefore arranged in the given pattern. Additional EAP layers, first electrode layers and second electrode layers may be formed such that each of a plurality of EAP layers are disposed between a layer of a first electrode and a layer of second electrodes, wherein the patterning of plurality of the second electrodes in each respective layer are aligned with the patterning of the second electrodes in the other respective layers. The sheet of the one or more EAP layers sandwiched between the layers of the first electrode and the layers of the second electrodes is then bent so that opposite edges of the sheet meet. The opposite edges are coupled together to form a catheter lumen 1510 through the formed sheet. Alternatively, a plurality of catheter may be formed from each sheet. In such case, the sheet is separate into a plurality of portions each used to form a catheter. Each portion may then be curled and the opposite edges coupled together to form the catheter.

Figure 16:
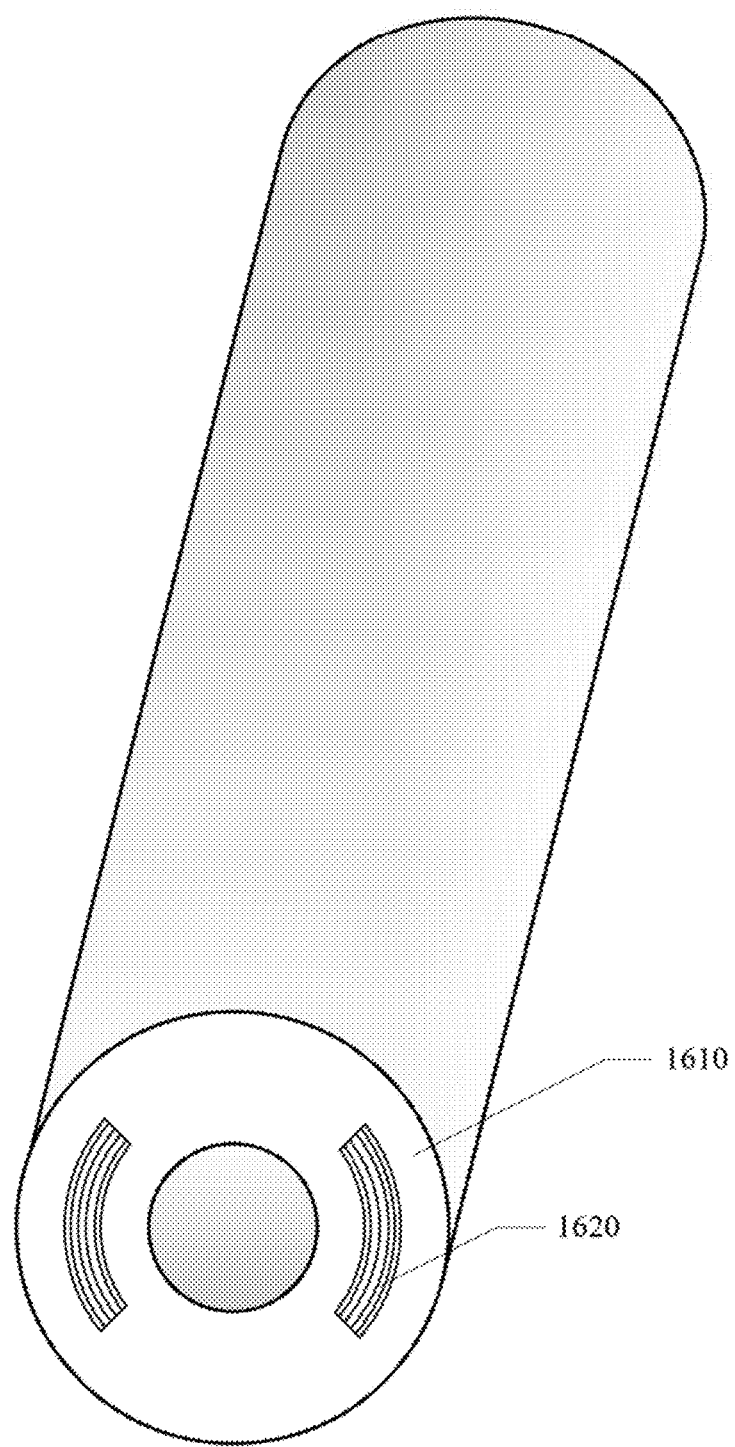
FIG. 16 shows a block diagram of a wire guide or catheter medical device, in accordance with yet another embodiment of the present technology.

Referring now to FIG. 16, a wire guide or catheter medical device, in accordance with yet another embodiment of the present technology, is shown. The wire guide or catheter may include a catheter body 1610 and a plurality of EAP constructs 1620. Each EAP construct may be a multi-layer EAP actuator. The multi-layer EAP actuator may include one or more layers of an EAP material, one or more layers of a first electrode and one or more layers of a second electrode. The one or more EAP layers are disposed between alternating ones of the first electrode and second electrode, in one implementation, each EAP construct may be molded into the wire guide or catheter body. In another implementation, each EAP construct may be inserted into pockets formed in the wire guide or catheter body.

The foregoing descriptions of specific embodiments of the present technology have been presented for purposes of illustration and description. They are not intended to be exhaustive or to limit the invention to the precise forms disclosed, and many modifications and variations are possible in light of the above teaching. The embodiments were chosen and described in order to best explain the principles of the present technology and its practical application, to thereby enable others skilled in the art to best utilize the present technology and various embodiments with various modifications as are suited to the particular use contemplated. It is intended that the scope of the invention be defined by the claims appended hereto and their equivalents.

What is claimed is:

1. A medical device in a guide wire form, comprising:
    one or more sections provided along the length of the guide wire form, divided lengthwise into one or more sections, each section comprising:
        one or more layers of a first electrode, wherein at least one of the layers of the first electrode includes a part of an electrode that extends an entire length of the guide wide form;
        one or more layers of a second electrode; and
        a plurality of electroactive polymer (EAP) layers, wherein each EAP layer is disposed between a layer of the first electrode and a layer of the second electrode, each EAP layer being activated by a voltage across the corresponding layer of the first electrode and the corresponding layer of the second electrode, and wherein the one or more layers of the first electrode, and wherein a first group of the EAP layers and the second group of the EAP layers are independently activated to cause a bending of the guide wire form in a predetermined direction or to achieve a predetermined shape for the guide wire form.

2. The medical device of claim 1, wherein each of the one or more layers of the second electrode include a plurality of second electrodes disposed in a given pattern.

3. The medical device of claim 1, wherein second electrodes in the same layer are aligned with each other.

4. The medical device of claim 1, wherein corresponding second electrodes in different layers are aligned with each other.

5. The medical device of claim 1, wherein the EAP comprises: at least one monomer of vinylidene-fluoride; at least one monomer selected from the group consisting of trifluoroethylene and tetrafluoroethylene; and at least one monomer selected from the group consisting of tetrafluoroethylene vinyl fluoride, perfluoro (methyl vinyl ether), bromotrifluoroethylene, chlorofluoroethylene, chlorotrifluoroethylene, and hexafluoropropylene.

6. The medical device of claim 1, wherein a portion of the medical device comprises:
    a first layer of the first electrode including a core;
    a first EAP layer conformally disposed on the first layer of the first electrode; and
    a first layer of the second electrode conformally disposed on the first EAP layer.

7. The medical device of claim 1, further comprising: an EAP layer disposed between a layer of the first electrode and a layer of the second electrode as a sheet rolled or folded into the guide wire form factor; and wherein a given pattern of the second electrode comprises a pattern in the direction that the sheet is rolled or folded such that portions of the second electrode are aligned in a stack.

8. The medical device of claim 1, wherein each of a plurality of the EAP layers are disposed between alternating layers of the first electrode and second electrode in a stack.

9. A medical device comprising:
    a guide wire including;
        one or more layers of a first electrode, wherein at least one of the layers of the first electrode includes an electrode that extends an entire length of the guide wide;
        one or more layers of a plurality of second electrodes; and
        a plurality of electroactive polymer layers, wherein each electroactive polymer layer is disposed between a layer of a first electrode and a layer of a plurality of second electrodes, each electroactive polymer layer being activated by a voltage across the corresponding layer of the first electrode and the corresponding layer of the second electrode, and wherein the one or more layers of the first electrode, the one or more layers of the plurality of second electrode and the plurality of electroactive polymer layers are arranged in a guide wire form, and wherein at least a first group of the electroactive polymer layers and the second group of the electroactive polymer layers are independently activated to cause a bending of the guide wire form in a predetermined direction or to achieve a predetermined shape for the guide wire form; and
    a drive unit coupled to the guide wire to generate one or more potential voltages and to apply each of the one or more potential voltages respectively across one or more sets of the first electrode and the second electrode.

10. The medical device of claim 9, wherein the guide wire further includes a core, wherein a stack of the plurality of electroactive polymer are disposed around at least a portion of the core.

11. The medical device of claim 9, wherein: a single electroactive polymer layer is disposed between a single layer of the first electrode and a single layer of the plurality of second electrodes as a sheet rolled or folded into the guide wire form factor; wherein a given pattern of the second electrodes comprises a geometrically expanding pattern in the direction that the sheet is rolled or folded such that corresponding second electrodes are radially aligned in a stack.

12. The medical device of claim 9, wherein the guide wire form includes a lumen through the one or more layers of the first electrode, the one or more layers of the plurality of second electrode and the plurality of electroactive polymer layers.

13. The medical device of claim 9, wherein the one or more potential voltages respectively applied across one or more sets of the first electrode and second electrode causes a deflection in the guide wire form.

14. The medical device of claim 9, wherein the one or more potential voltages respectively applied across one or more sets of the first electrode and second electrode causes a change in the rigidity of the guide wire form.

15. A device comprising:
    a guide wire including a plurality of active EAP portions arranged in multiple stacks, wherein the active EAP portions in each stack are aligned with each other, each EAP portion comprising an EAP layer between a layer of a first electrode and a layer of a second electrode, each EAP layer being activated by a voltage across the corresponding layer of first electrode and the corresponding layer of the second electrode, and wherein a first stack of the active EAP portions and the second stack of the active EAP portions are independently activated to cause a bending of the guide wire in a predetermined direction or to achieve a predetermined shape for the guide wire, wherein an electrode in a layer of the first electrode extends an entire length of the guide wide; and a drive unit, coupled to the guide wire, to generate one or more potential voltages and applied to each of the one or more generated voltages to one or more active EAP portions to control one or more physical parameters of the guide wire.

16. The device according to claim 15, wherein the one or more generated voltages applied by the drive unit to the one or more active EAP portions of the guide wire control a deflection of the guide wire.

17. The device according to claim 15, wherein the one or more generated voltages applied by the drive unit to the one or more active EAP portions of the guide wire control a rigidity of the guide wire.

18. The device according to claim 15, wherein the guide wire comprises:
a core;
a first layer of the first electrode formed on the core;
a first layer of EAP formed on the first layer of the first electrode;
a first layer of a plurality of the second electrodes formed on the first layer of EAP;
a second layer of EAP formed on the first layer of the plurality of the second electrodes; and
a second layer of the first electrode formed on the second layer of EAP.

19. The device according to claim 15, wherein the guide wire comprises a rolled or folded sheet including: a layer of a first electrode disposed on a first side of a electroactive polymer layer; and a layer of a plurality of second electrodes disposed on a second side of the EAP layer, wherein the plurality of second electrodes are arranged in a geometrically expanding pattern in a direction that the sheet is rolled or folded.

20. The device according to claim 15, wherein the EAP comprises: at least one monomer of vinylidene-fluoride; at least one monomer selected from the group consisting of trifluoroethylene and tetrafluoroethylene; and at least one monomer selected from the group consisting of tetrafluoroethylene vinyl fluoride, perfluoro (methyl vinyl ether), bromotrifluorethylene, chlorofluoroethylene, chlorotrifluoroethylene, and hexafluoropropylene.

* * * * *